United States Patent
Ito

(10) Patent No.: US 11,472,865 B2
(45) Date of Patent: Oct. 18, 2022

(54) IGG-BINDING PEPTIDE, AND SPECIFIC MODIFICATION OF ANTIBODY WITH SAID PEPTIDE

(71) Applicant: Kagoshima University, Kagoshima (JP)

(72) Inventor: Yuji Ito, Kagoshima (JP)

(73) Assignee: Kagoshima University, Kagoshima (JP)

( * ) Notice: Subject to any disclaimer, the term of this patent is extended or adjusted under 35 U.S.C. 154(b) by 56 days.

(21) Appl. No.: 16/620,715

(22) PCT Filed: May 18, 2018

(86) PCT No.: PCT/JP2018/019287
§ 371 (c)(1),
(2) Date: Dec. 9, 2019

(87) PCT Pub. No.: WO2018/230257
PCT Pub. Date: Dec. 20, 2018

(65) Prior Publication Data
US 2021/0147512 A1    May 20, 2021

(30) Foreign Application Priority Data
Jun. 16, 2017 (JP) .............................. JP2017-118735

(51) Int. Cl.
*C07K 16/00* (2006.01)
*C07K 14/00* (2006.01)

(52) U.S. Cl.
CPC ............ *C07K 16/00* (2013.01); *C07K 14/001* (2013.01); *C07K 2317/52* (2013.01); *C07K 2317/92* (2013.01); *C07K 2317/94* (2013.01)

(58) Field of Classification Search
CPC .................................................. C07K 14/001
See application file for complete search history.

(56) References Cited

U.S. PATENT DOCUMENTS 6,013,763 A    1/2000    Braisted et al.

FOREIGN PATENT DOCUMENTS

| EP | 3299383 A1 | 3/2018 |
| WO | WO 2016/186206 A1 | 11/2016 |
| WO | WO 2018/199337 | * 11/2018 |

OTHER PUBLICATIONS

VOET. Fundamentals of Biochemistry, 2013, 77-84. (Year: 2013).*
International Search Report dated Aug. 7, 2018, in PCT/JP2018/019287.
54th Annual Japanese Peptide Symposium, Poster Presentation No. P-136, "A novel covalently-labeling method of IgG by using protein A-mimic peptide," Nov. 20, 2017.
Axup et al., "Synthesis of site-specific antibody-drug conjugates using unnatural amino acids," PNAS, Oct. 2, 2012, 109(40):16101-16106.
Bernardes et al., "Site-specific chemical modification of antibody fragments using traceless cleavable linkers," Nature Protocols, 2013, 8(11):2079-2089.
Dennler et al., "Transglutaminase-Based Chemo-Enzymatic Conjugation Approach Yields Homogeneous Antibody-Drug Conjugates," Bioconjugate Chemistry, 2014, 25:569-578.
Hashida et al., "More Useful Maleimide Compounds for the Conjugation of Fab' to Horseradish Peroxidase through Thiol Groups in the Hinge," Journal of Applied Biochemistry, 1984, 6:56-63.
Hermanson, G.T., Bioconjugate Techniques, 3rd Ed., Elsevier, USA, 2013, 726-739.
Himeno et al., "A Novel Covalently-Labeling Method of IGG by Using Protein A-Mimic Peptide," Proceedings of the 54th Japanese Peptide Symposium, Oct. 20, 2017, p. 184, p. 136.
Imagawa et al., "Characteristics and Evaluation of Antibody-Horseradish Peroxidase Conjugates Prepared by Using a Maleimide Compound, Glutaraldehyde, and Periodate," Journal of Applied Biochemistry, 1982, 4:41-57.
Jeger et al., "Site-Specific and Stoichiometric Modification of Antibodies by Bacterial Transglutaminase," Angewandte Chemie Int. Ed., 2010, 49:9995-9997.
Rodwell et al., "Site-specific covalent modification of monoclonal antibodies: In vitro and in vivo evaluations," Proc. Natl. Acad. Sci. USA, Apr. 1986, 83:2632-2636.
Shen et al., "Conjugation site modulates the in vivo stability and therapeutic activity of antibody-drug conjugates," Nature Biotechnology, Feb. 2012, 30(2):184-189.
Tian et al., "A general approach to site-specific antibody drug conjugates," PNAS, Feb. 4, 2014, 111(5):1766-1771.
Zimmerman et al., "Production of Site-Specific Antibody-Drug Conjugates Using Optimized Non-Natural Amino Acids in a Cell-Free Expression System," Bioconjugate Chemistry, 2014, 25:351-361.

* cited by examiner

*Primary Examiner* — Noble E Jarrell
(74) *Attorney, Agent, or Firm* — Foley & Lardner LLP

(57) ABSTRACT

It is an object of the present invention to provide a method for modifying an antibody in a specific and simple manner, and others. The present invention relates to: an IgG-binding peptide, an IgG-binding peptide modified with a crosslinking agent, a complex of an IgG-binding peptide modified with the crosslinking agent and IgG, a method for producing the complex, and others.

18 Claims, 8 Drawing Sheets
Specification includes a Sequence Listing.

(A)

(B)

IGG-BINDING PEPTIDE, AND SPECIFIC MODIFICATION OF ANTIBODY WITH SAID PEPTIDE

CROSS-REFERENCE TO RELATED APPLICATIONS

This application is the U.S. National Stage of PCT/JP2018/019287, filed May 18, 2018, which claims priority to JP 2017-118735, filed Jun. 16, 2017.

The instant application contains a Sequence Listing which has been submitted in ASCII format via EFS-WEB and is hereby incorporated by reference in its entirety. Said ASCII copy, created on Dec. 4, 2019, is named sequence.txt and is 6,501 bytes.

TECHNICAL FIELD

The present invention relates to an IgG-binding peptide, an IgG-binding peptide modified with a cross-linking agent, a conjugate of the IgG-binding peptide modified with the cross-linking agent and IgG, and a method for producing the conjugate, etc.

BACKGROUND ART

Antibodies have heretofore been often utilized in the detection of target molecules in various research and development activities, and are also of great industrial importance as detection reagents or diagnostic drugs. The antibodies have also received attention as drugs for the treatment of diseases because of their specificity for target molecules.

Chemical modifications for the functionalization of antibodies have been practiced, including modification with an enzyme such as alkaline phosphatase (AP) or peroxidase (HRP) (Non Patent Literatures 1 and 2), iodation or addition of a chelating compound for radioisotopes (Non Patent Literature 3), and modification with a low-molecular compound such as biotin (Non Patent Literature 4). These modifications are typically performed via a lysine amino group, a cysteine thiol group, and an activated carboxyl group, etc. These modifications are specific for the functional groups, but are not site-specific. Therefore, the problems of these approaches include, for example, reduction in the activity of antibodies due to the modification or the like of the antigen-binding sites of the antibodies. When the number of ligands to be introduced is increased to improve the detection sensitivity or therapeutic effect, the physical property or structure of the antibody may vary as the number of amino acid residues to be modified increase. This decreases the activity of the antibody or causes non-specific binding, resulting in the decrease of the therapeutic effect, detection sensitivity or specificity.

In order to overcome these problems, antibody modification has been practiced using antibodies having a particular site-specifically introduced functional group. For example, modification at a particular site is achieved by introducing a non-natural amino acid (Non Patent Literatures 5 to 7) or free cysteine (Non Patent Literatures 8 and 9) to the particular site by genetic manipulation. Also, it has been reported that modification targeting particular natural or artificially introduced glutamine in antibodies is performed by using transglutaminase (TG) (Non Patent Literatures 10 and 11). It is however known that the reaction yields are largely influenced by the structure of a compound to be introduced or the spatial environment of the targeted glutamine residue. Although site-specific antibody modification techniques are under development as mentioned above, these methods often require engineering antibodies themselves and are not always advantageous in light of reduction in the functions of the antibodies and high development cost in association with the engineering.

CITATION LIST

Non Patent Literature

Non Patent Literature 1: Imagawa, M. et al., Journal of Applied Biochemistry, 1982, 4, pp. 41-57
Non Patent Literature 2: Hashida, S et al., Journal of Applied Biochemistry, 1984, 6, pp. 56-63
Non Patent Literature 3: Rodwell, J. D. et al., Proceedings of the National Academy of Sciences of the United States of America, 1986, 83, pp. 2632-2636
Non Patent Literature 4: Hermanson, G. T., Bioconjugate Techniques, The third edition, Elsevier, USA, 2013
Non Patent Literature 5: Axup, J. Y. et al., Proceedings of the National Academy of Sciences of the United States of America, 2012, 109, pp. 16101-16106
Non Patent Literature 6: Tian, F. et al., Proceedings of the National Academy of Sciences of the United States of America, 2014, 111, pp. 1766-1771
Non Patent Literature 7: Zimmerman, E. S. et al., Bioconjugate chemistry, 2014, 25, pp. 351-361
Non Patent Literature 8: Shen, B. Q. et al., Nature Biotechnology, 2012, 30, pp. 184-189
Non Patent Literature 9: Bernardes, G. J. et al., Nature Protocols, 2013, 8, pp. 2079-2089
Non Patent Literature 10: Dennler, P. et al., Bioconjugate Chemistry, 2014, 25, pp. 569-578
Non Patent Literature 11: Jeger, S. et al., Angewandte Chemie 2010, 49, pp. 9995-9997

SUMMARY OF INVENTION

Technical Problem

Accordingly, there is a demand for methods that can modify antibodies specifically and conveniently.

Solution to Problem

The present inventor has prepared a IgG-binding peptide, and found that the IgG antibody may be modified with the peptide without decreasing the activity of the IgG antibody, and completed the present invention.

Therefore, the present invention encompasses the following aspects.

(1) A peptide, IgG-binding peptide, or peptide for use in binding to IgG, comprising:

(SEQ ID NO: 1)
(Xaa1)NMQCQRRFYEALHDPNLNEEQRNA(Xaa2)I(Xaa3)SIRDDC, (SEQ ID NO: 2)
(Xaa4)FNMQCQRRFYEALHDPNLNEEQRNA(Xaa2)I(Xaa3)SIRDD
C, or the amino acid sequence of SEQ ID NO: 1 or 2 in which one or several amino acids are added, deleted, and/or substituted at positions other than Xaa1 to Xaa4;
wherein Xaa1 is selected from the group consisting of a lysine residue, an ornithine residue, a cysteine residue, an aspartic acid residue, a glutamic acid residue, a 2-aminosuberic acid residue, and a diaminopropionic acid residue;

Xaa2 and Xaa3 are each independently selected from the group consisting of an arginine residue, a histidine residue, an aspartic acid residue, a glutamic acid residue, a serine residue, a threonine residue, an asparagine residue, a glutamine residue, a tyrosine residue, and a cysteine residue; and Xaa4 is selected from the group consisting of a glycine residue, an alanine residue, a valine residue, a leucine residue, an isoleucine residue, a methionine residue, a proline residue, a phenylalanine residue, a tryptophan residue, a lysine residue, an ornithine residue, a cysteine residue, an aspartic acid residue, a glutamic acid residue, a β-alanine residue, a 2-aminosuberic acid residue, a diaminopropionic acid residue, and $NH_2$—(PEG)n-CO (n=1 to 50), or absent.

(2) The peptide according to (1), wherein Xaa1 is selected from the group consisting of a lysine residue, an ornithine residue, a cysteine residue, and a diaminopropionic acid residue.

(3) The peptide according to (2), wherein Xaa1 is a lysine residue.

(4) The peptide according to any one of (1) to (3), wherein Xaa4 is selected from the group consisting of a glycine residue, an alanine residue, a β-alanine residue, and $NH_2$—(PEG)n-CO (n=1 to 50), or absent.

(5) The peptide according to (4), wherein Xaa4 is a glycine residue, or absent.

(6) The peptide according to any one of (1) to (5), wherein Xaa2 and Xaa3 are each independently selected from the group consisting of an arginine residue, a histidine residue, and a glutamic acid residue.

(7) The peptide according to (6), wherein Xaa2 and Xaa3 are an arginine residue.

(8) The peptide according to any one of (1) to (7), wherein the cysteine residue at position 5 and the cysteine residue at position 34 in SEQ ID NO: 1, and the cysteine residue at position 6 and the cysteine residue at position 35 in SEQ ID NO: 2 are linked via a disulfide bond or a linker.

(9) The peptide according to any one of (1) to (8), comprising the amino acid sequence of:

```
                                      (SEQ ID NO: 9)
FNMQCQRRFYEALHDPNLNEEQRNARIRSIRDDC, (SEQ ID NO: 7)
GFNMQCQRRFYEALHDPNLNEEQRNARIRSIRDDC, (SEQ ID NO: 4)
KNMQCQRRFYEALHDPNLNEEQRNARIRSIRDDC, (SEQ ID NO: 5)
GFNMQCQKRFYEALHDPNLNEEQRNARIRSIRDDC, (SEQ ID NO: 6)
KNMQCQKRFYEALHDPNLNEEQRNARIRSIRDDC, (SEQ ID NO: 10)
FNMQQQRRFYEALHDPNLNEEQRNARIRSIRDD,
or (SEQ ID NO: 11)
GKNMQCQRRFYEALHDPNLNEEQRNARIRSIRDDC.
```

(10) The peptide according to any one of (1) to (9), to which a labeling substance or a drug is bound.

(11) The peptide according to any one of (1) to (10), wherein R at position 7 in SEQ ID NO: 1 or R at position 8 in SEQ ID NO: 2 is substituted with a lysine residue, or further comprising a lysine residue at the C-terminus of SEQ ID NO: 1 or SEQ ID NO: 2.

(12) The peptide according to (11), wherein the labeling substance or drug is bound to the substituted lysine residue or the C-terminal lysine residue.

(13) The peptide according to any one of (1) to (12), wherein the N-terminal amino acid is acetylated or aminated.

(14) The peptide according to any one of (1) to (13), wherein the C-terminal amino acid is amidated.

(15) The binding peptide according to any one of (1) to (14), wherein Xaa1 and Xaa4 are modified with a crosslinking agent, or if Xaa4 is absent, the phenylalanine at position 1 in SEQ ID NO: 2 is modified with a crosslinking agent.

(16) The peptide according to (15), wherein the crosslinking agent is selected from the group consisting of DSG (disuccinimidyl glutarate), DSS (disuccinimidyl suberate), DMA (dimethyl adipimidate dihydrochloride), DMP (dimethyl pimelimidate dihydrochloride), DMS (dimethyl suberimidate dihydrochloride), DTBP (dimethyl 3,3'-dithiobispropionimidate dihydrochloride) and DSP (dithiobis(succinimidyl propionate)).

(17) The peptide according to (16), wherein the crosslinking agent is DSG (disuccinimidyl glutarate) or DSS (disuccinimidyl suberate).

(18) A crosslinked complex of the peptide according to any one of (15) to (17) and IgG.

(19) A method for producing a complex of peptide and IgG, comprising mixing the peptide according to any one of (15) to (17) with IgG, thereby crosslinking the peptide modified with the crosslinking agent to IgG.

(20) A pharmaceutical composition comprising the peptide according to any one of (1) to (17) or the complex according to (18).

The present specification encompasses the contents disclosed in Japanese Patent Application No. 2017-118735 to which of the present application claims priority.

An IgG-binding peptide modified with the crosslinking agent of the present invention may be added to IgG in a short time with no or little side reaction. Therefore, IgG may be specifically and conveniently modified with various compounds by attaching the various compounds to the IgG binding peptide.

BRIEF DESCRIPTION OF DRAWINGS

As shown in FIG. 1A, in the conventional method, a functional ligand such as a labeling substance or a drug binds to a random site of an antibody. As shown in FIG. 1B, in the method of one embodiment of the present invention, a functional ligand such as a labeling substance or a drug binds site-specifically to an antibody via an IgG-binding peptide.

FIG. 4A shows the results of the SDS-PAGE for human IgG1 (Trastuzumab) of lane 1, the reaction product of human IgG1 and αZ34C 7K of lane 2, human IgG2 of lane 3, the reaction product of human IgG2 and αZ34C 7K of lane 4, human IgG3 of lane 5, the reaction product of human IgG3 and αZ34C 7K of lane 6, human IgG4 of lane 7, and the reaction product of human IgG4 and αZ34C 7K of lane 8. Lanes 1 to 8 in FIG. 4B correspond to lanes 1 to 8 in FIG. 4A. FIG. 4C shows the results of the SDS-PAGE for mouse IgG1 of lane 1, the reaction product of mouse IgG1 and αZ34C 7K of lane 2, mouse IgG2b of lane 3, the reaction product of mouse IgG2b and αZ34C 7K of lane 4, mouse IgG3 of lane 5, and the reaction product of mouse IgG3 and αZ34C 7K of lane 6. FIG. 4D shows the results of the SDS-PAGE for rabbit IgG of lane 1, the reaction product of rabbit IgG and αZ34C 7K of lane 2, rat IgG1 of lane 3, the reaction product of rat IgG1 and αZ34C 7K of lane 4, rat IgG2b of lane 5, the reaction product of rat IgG2b and αZ34C 7K of lane 6, rat IgG2c of lane 7, and the reaction product of rat IgG2c and αZ34C 7K of lane 8.

FIG. 5A shows the results of the SDS-PAGE for human IgG1 (Trastuzumab) of lane 1, the reaction product of human IgG1 and εZ34C 7K of lane 2, human IgG2 of lane 3, the reaction product of human IgG2 and εZ34C 7K of lane 4, human IgG3 of lane 5, the reaction product of human IgG3 and εZ34C 7K of lane 6, human IgG4 of lane 7, and the reaction product of human IgG4 and εZ34C 7K of lane 8. FIG. 5B shows the results of the SDS-PAGE for mouse IgG1 of lane 1, the reaction product of mouse IgG1 and εZ34C 7K of lane 2, mouse IgG2b of lane 3, the reaction product of mouse IgG2b and εZ34C 7K of lane 4, mouse IgG3 of lane 5, and the reaction product of mouse IgG3 and εZ34C 7K of lane 6. FIG. 5C shows the results of the SDS-PAGE for rabbit IgG of lane 1, the reaction product of rabbit IgG and εZ34C 7K of lane 2, rat IgG1 of lane 3, the reaction product of rat IgG1 and εZ34C 7K of lane 4, rat IgG2b of lane 5, the reaction product of rat IgG2b and εZ34C 7K of lane 6, rat IgG2c of lane 7, and the reaction product of rat IgG2c and εZ34C 7K of lane 8.

DESCRIPTION OF EMBODIMENTS

<IgG-Binding Peptide>

Figure 1:
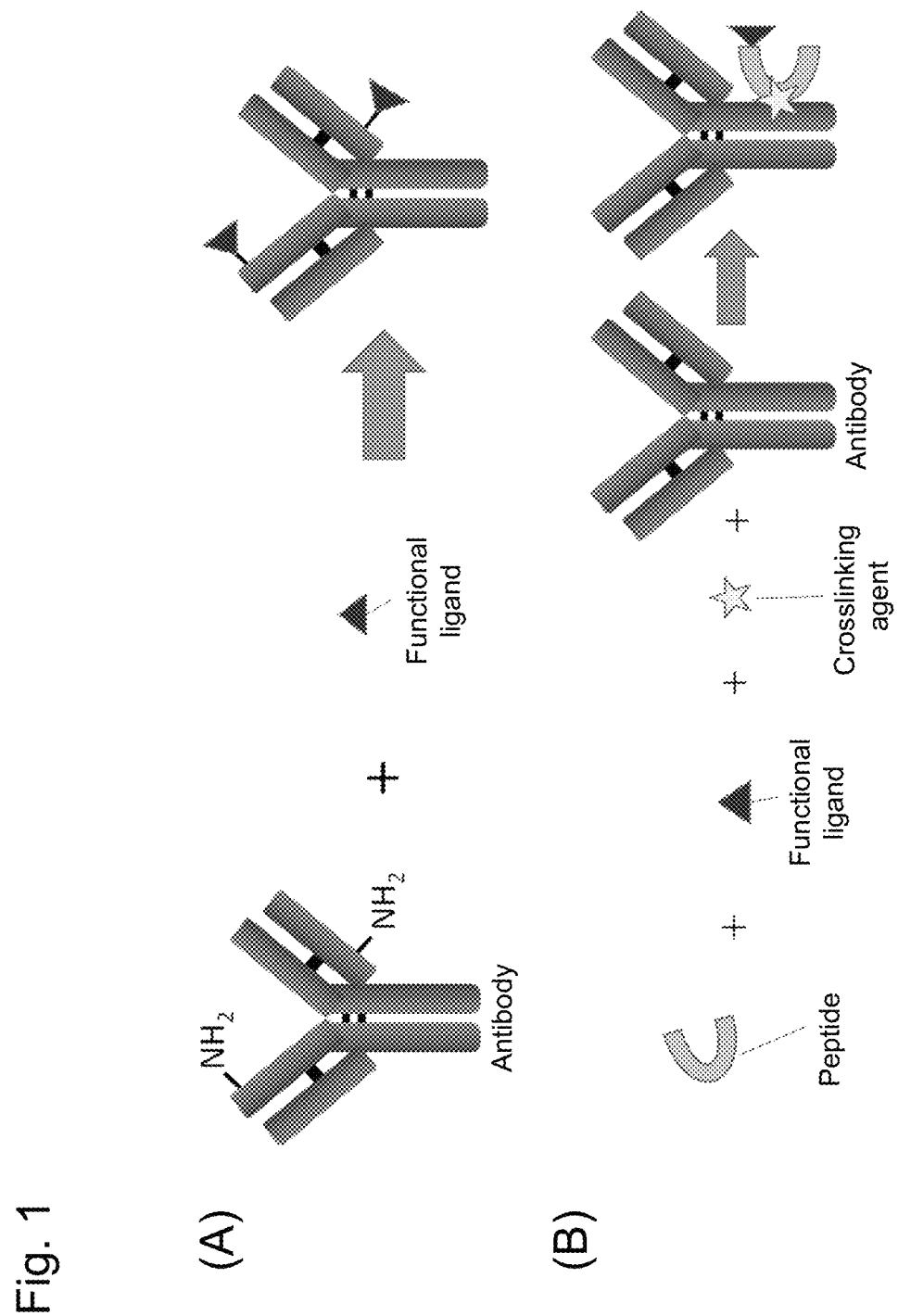
FIG. 1A shows a schematic diagram of random labeling such as the amine coupling method, which is a conventional method for labeling antibodies.
FIG. 1B shows the site-specific labeling according to the method of one embodiment of the present invention.

"IgG" as used in the present specification refers to IgG of mammals, for example primates such as humans and chimpanzees, laboratory animals such as rats, mice, and rabbits, and livestock animals such as pigs, cows, horses, sheep, and goats, and also IgG of pet animals such as dogs and cats, and preferably IgG of humans, mice, rats, or rabbits, further preferably of rats or mice. Examples of IgG subclasses include, but are not limited to, human IgG1, IgG2, IgG3, IgG4 (preferably human IgG1, IgG2, or IgG4), mouse IgG1, mouse IgG2a, mouse IgG2b, mouse IgG3 (preferably mouse IgG2a, mouse IgG2b, mouse IgG3), rat IgG1, rat IgG2a, rat IgG2b, rat IgG3 (preferably rat IgG1 or rat IgG2c), and rabbit IgG.

In one aspect, the present invention relates to a peptide comprising the amino acid sequence of (Xaa1)NMQCQRRFYEALHDPNLNEEQRNA(Xaa2)I(Xaa3)SIRDDC (SEQ ID NO: 1) or (Xaa4)FNMQCQRRF-YEALHDPNLNEEQRNA(Xaa2)I(Xaa3)SIRDDC (SEQ ID NO: 2), or the amino acid sequence of SEQ ID NO: 1 or 2 in which one or several amino acids are added, deleted, and/or substituted at positions other than Xaa1 to Xaa4. The peptide of the present invention is preferably an IgG-binding peptide or a peptide for use in binding to IgG. The amino acid sequence of SEQ ID NO: 1 or SEQ ID NO: 2 may be a Z34C peptide (Braisted AC. and Wells JA. Proc. Natl. Acad. Sci. USA, 93, pp. 5688-5692, 1996) having optimized affinity by minimizing the IgG-binding domain (B-domain) of protein A and introducing mutations and the like, and having mutations at Xaa1 to Xaa4.

In the above amino acid sequence, Xaa1 is selected from the group consisting of a lysine residue, an ornithine residue, a cysteine residue, an aspartic acid residue, a glutamic acid residue, a 2-aminosuberic acid residue, and a diaminopropionic acid residue, preferably from the group consisting of a lysine residue, an ornithine residue, a cysteine residue, and a diaminopropionic acid residue, and is further preferably a lysine residue. Moreover, in the above amino acid sequence, Xaa2 and Xaa3 are each independently selected from the group consisting of an arginine residue, a histidine residue, an aspartic acid residue, a glutamic acid residue, a serine residue, a threonine residue, an asparagine residue, a glutamine residue, a tyrosine residue and a cysteine residue, preferably from the group consisting of an arginine residue, a histidine residue, and a glutamic acid residue, and is further preferably an arginine residue. In one embodiment, Xaa2 and Xaa3 are not reactive towards the crosslinking agents described below. Moreover, in the above amino acid sequence, Xaa4 is selected from the group consisting of a glycine residue, an alanine residue, a valine residue, a leucine residue, an isoleucine residue, a methionine residue, a proline residue, a phenylalanine residue, a tryptophan residue, a lysine residue, an ornithine residue, a cysteine residue, an aspartic acid residue, a glutamic acid residue, a β-alanine residue, a 2-aminosuberic acid residue, a diaminopropionic acid residue, and $NH_2$—(PEG)n-CO (n=1 to 50, 1 to 20, 1 to 10, and preferably n=1 to 7), or absent. Xaa4 is preferably selected from the group consisting of a glycine residue, an alanine residue, a β-alanine residue, and $NH_2$—(PEG)n-CO (n=1 to 50) or absent, and is further preferably a glycine residue or absent.

Specific examples of the amino acid sequence of SEQ ID NO: 1 include the amino acid sequence of KNMQCQRRF-YEALHDPNLNEEQRNARIRSIRDDC (SEQ ID NO: 4), and specific examples of the amino acid sequence of SEQ ID NO: 2 include the amino acid sequence of GFNMQCQRRF-YEALHDPNLNEEQRNARIRSIRDDC (SEQ ID NO: 7). In addition, specific examples of the amino acid sequence of SEQ ID NO: 1 in which one or several amino acids are added, deleted, and/or substituted include the amino acid sequence of KNMQCQKRFYEALHDPNLNEEQR-NARIRSIRDDC (SEQ ID NO: 6), obtained by substitution of the arginine residue with a lysine residue at position 7 of the amino acid sequence of SEQ ID NO: 4, and specific examples of the amino acid sequence of SEQ ID NO: 2 in which one or several amino acids are added, deleted, and/or substituted include the amino acid sequence of GFNMQCQKRFYEALHDPNLNEEQRNARIRSIRDDC (SEQ ID NO: 5), obtained by substitution of the arginine residue with a lysine residue at position 8 of the amino acid sequence of SEQ ID NO: 7.

The range of "one or several" used herein of amino acids that may be added, deleted, and/or substituted in the amino acid sequence of SEQ ID NO: 1 or 2 is, for example, 1 to 5, 1 to 4, preferably 1 to 3, 1 to 2, and further preferably 1.

When an amino acid is added or substituted in SEQ ID NO: 1 or SEQ ID NO: 2, the amino acid inserted by the addition or substitution is preferably not a cysteine residue. Moreover, when the amino acid inserted by addition or substitution is a lysine residue, the ε amino group of the lysine residue is preferably modified and not reactive towards the crosslinking agents described below. In addition, when an amino acid is deleted or substituted in SEQ ID NO: 1 or SEQ ID NO: 2, the deleted or substituted amino acid is preferably not a cysteine residue.

Additions, deletions, and/or substitutions to the amino acid sequence of SEQ ID NO: 1 or 2 may be performed on amino acids that do not significantly affect the binding of the peptide to IgG. Examples of such additions, deletions and/or substitutions to amino acids include the deletion or substitution of the arginine residue at position 7 of the amino acid sequence of SEQ ID NO: 1 and the arginine residue at position 8 of the amino acid sequence of SEQ ID NO: 2, and the addition of a lysine residue to the C-terminus of SEQ ID NO: 1 or SEQ ID NO: 2. An amino acid suitable for substitution may be appropriately determined, taking the properties of the side chain into consideration, for example, based on conservative amino acid substitution.

Examples of the amino acid sequence of SEQ ID NO: 1 or 2 include, but are not limited to, the amino acid sequence of

```
                                        (SEQ ID NO: 9)
FNMQCQRRFYEALHDPNLNEEQRNARIRSIRDDC, (SEQ ID NO: 7)
GFNMQCQRRFYEALHDPNLNEEQRNARIRSIRDDC, (SEQ ID NO: 4)
KNMQCQRRFYEALHDPNLNEEQRNARIRSIRDDC, (SEQ ID NO: 5)
GFNMQCQKRFYEALHDPNLNEEQRNARIRSIRDDC, (SEQ ID NO: 6)
KNMQCQKRFYEALHDPNLNEEQRNARIRSIRDDC, (SEQ ID NO: 10)
FNMQQQRRFYEALHDPNLNEEQRNARIRSIRDD,
and (SEQ ID NO: 11)
GKNMQCQRRFYEALHDPNLNEEQRNARIRSIRDDC.
```

The two cysteine residues of the amino acid sequence of SEQ ID NO: 1 or 2, that is, the cysteine residue at position 5 and the cysteine residue at position 34 in SEQ ID NO: 1, and the cysteine residue at position 6 and the cysteine residue at position 35 in SEQ ID NO: 2, may be linked via a disulfide bond or a linker to form a cyclic peptide.

Preferably, in the amino acid sequence of SEQ ID NO: 1 or 2, the two cysteine residues form a disulfide bond. When the two cysteine residues of the amino acid sequence of SEQ ID NO: 1 or 2 are linked by a linker, examples of the type of the linker include, but are not particularly limited to, a linker represented by a formula selected from the group consisting of the following formulae:

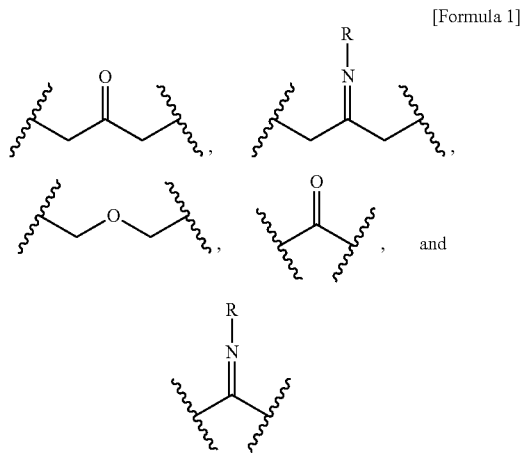

[Formula 1]

The linker is preferably a linker represented by:

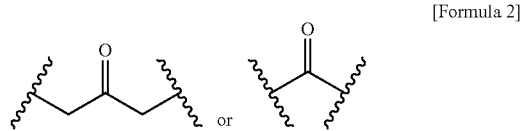

[Formula 2]

and further preferably a linker represented by:

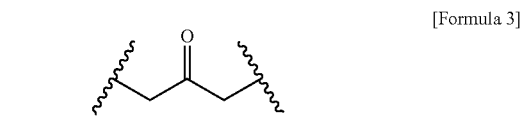 [SMILES: *CC(=O)C*]

[Formula 3]

The R in the linker in the above IgG-binding peptide is a substituted or unsubstituted alkyl, preferably substituted or unsubstituted C1 to C6 alkyl, that is, a methyl group, an ethyl group, a propyl group, a butyl group, a pentyl group or a hexyl group. Examples of the substituent for R include, but are not particularly limited to, a hydroxy group, a (mono or poly)ethylene oxide group, a carboxyl group, an alkoxy group, an acyl group, an alkyl group, an amide group, an ester group, a halogen group (F, Cl, Br, or I), or a combination thereof. Moreover, the wavy line portion in the formulae means the binding portion with a sulfide group. This linker is more excellent in stability, for example, resistance to alkali or resistance to reduction reaction or the like, preferably resistance to alkali, than a normal disulfide bond.

The method for preparing a peptide having the above linker is not particularly limited. For example, a peptide having a linker represented by the following formulae:

[Formula 4]

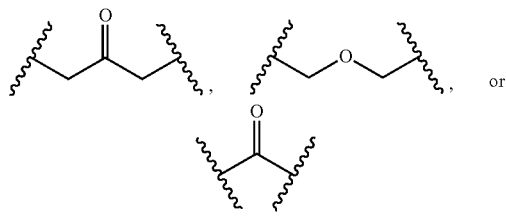

may be obtained, for example, by the following method:

a method comprising mixing a peptide containing two cysteine residues with a compound having a reactive functional group (for example, a halogen group, an imidazole group, and the like) involved in the crosslinking reaction on the wavy line portion of the above linker, for example, under acidic conditions.

Furthermore, by reacting the peptide having the above carbonyl group with a primary amine ($RNH_2$), a peptide linked by a linker represented by:

[Formula 5]

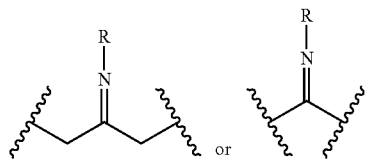

may be obtained (R has the same meaning as described above).

In the compound, the halogen group is preferably selected from the group consisting of F, Cl, Br, and I, further preferably Cl, Br, and I. The halogen groups are preferably the same, and further preferably all halogen groups are Cl.

As described above, in the peptide having the amino acid sequence of SEQ ID NO: 1, Xaa1 may be either a protein-constituting amino acid such as a lysine residue, an ornithine residue, a cysteine residue, an aspartic acid residue, or a glutamic acid residue, or a non-protein-constituting amino acid such as a diaminopropionic acid residue or a 2-aminosuberic acid residue, and is preferably a lysine residue, an ornithine residue, a cysteine residue or a diaminopropionic acid residue, and further preferably a lysine residue. Xaa1 is preferably modifiable by a crosslinking agent described later. The "non-protein-constituting amino acid" used herein refers to an amino acid that is not used to constitute a protein in an organism. For enhancing site specificity in the modification of the peptide of the present invention with a crosslinking agent, the α-amino group of Xaa1 in the amino acid sequence of SEQ ID NO: 1 is preferably modified with an acyl group such as an acetyl group or a propynyl group (the "acyl group" used herein is represented by the general formula: R—CO—, wherein R is a hydrocarbon, preferably an alkyl group having 1 to 6 carbon atoms), or with an amino group or the like. In addition, for enhancing site specificity in the modification of the peptide of the present invention with a crosslinking agent, the peptide of the present invention has preferably no or little (for example, only one or two) amino acid residue that is the same as Xaa1 in that sequence, and when it has the same amino acid residues as Xaa1, the amino acid residue is preferably modified so that the crosslinking agent does not react. In this case, an example of the modification of the same amino acid residue as Xaa1 may be, but is not limited to, the linking of a labeling substance or a drug as described in detail below. For example, when Xaa1 is a lysine residue, the peptide of the present invention has preferably no or little lysine residue at a position other than Xaa1 in the sequence, and when it has a lysine residue, the ε-amino group of the lysine residue is preferably modified.

Moreover, as described above, in the peptide having the amino acid sequence of SEQ ID NO: 2, Xaa4 may be either a protein-constituting amino acid such as a glycine residue, an alanine residue, a valine residue, a leucine residue, an isoleucine residue, a methionine residue, a proline residue, a phenylalanine residue, a tryptophan residue, a lysine residue, an ornithine residue, a cysteine residue, an aspartic acid residue or a glutamic acid residue, or a non-protein-constituting amino acid such as a β-alanine residue, a 2-aminosuberic acid residue, a diaminopropionic acid residue or $NH_2$—(PEG)n-CO (n=1 to 50, 1 to 20, 1 to 10, and preferably n=1 to 7), or it may be absent. Xaa4 is preferably a glycine residue, an alanine residue, a 3-alanine residue, or $NH_2$—(PEG)n-CO (n=1 to 50, 1 to 20, 1 to 10, and preferably n=1 to 7), and is further preferably a glycine residue or absent. Xaa4, or the N-terminal amino acid such as phenylalanine at position 1 when Xaa4 is absent is preferably modifiable by a crosslinking agent described later. For enhancing site specificity in the modification of the peptide of the present invention with a crosslinking agent, the α-amino group of Xaa4 (or the N-terminal amino acid such as phenylalanine at position 1 when Xaa4 is absent,) in the amino acid sequence of SEQ ID NO: 2 is preferably unmodified, and this α-amino group is preferably modified with a crosslinking agent. In addition, for enhancing site specificity in the modification of the peptide of the present invention with a crosslinking agent, the amino acid sequence of SEQ ID NO: 2 has preferably no or little (for example, only one or two) amino acid that may be modified with a crosslinking agent, and when it has an amino acid that may be modified with a crosslinking agent, the amino acid residue is preferably modified so that the crosslinking agent does not react. In this case, an example of the modification of the amino acid may be, but is not limited to, the linking of a labeling substance or a drug described in detail below. For example, it is preferable that the amino acid sequence of SEQ ID NO: 2 have no or little (for example, only one or two) lysine residue, and when it has a lysine residue, the ε-amino group of the lysine residue is preferably modified.

In addition, the IgG-binding peptide according to the present specification may be modified by, for example, by N-terminal acylation (for example, acetylation), amination, and/or PEGylation (polyethylene glycol addition), C-terminal amidation or the like, to improve the stability. When PEGylation is performed, the number of PEG molecules is not particularly limited, and for example, 1 to 50 molecules, 1 to 20 molecules, 2 to 10 molecules, 2 to 6 molecules, or 4 molecules of PEG can be added.

The peptide of the present invention has approximately 10 or more times, preferably approximately 50 or more times, more preferably approximately 200 or more times higher binding affinity for IgG compared with other immunoglobulins (IgA, IgE, and IgM). A dissociation constant (Kd) as to the binding of the peptide of the present invention to human IgG may be determined by surface plasmon resonance spectroscopy (using, for example, BIACORE system) and is, for example, $1 \times 10^{-1}$ M to less than $1 \times 10^{-3}$ M, preferably less than $1 \times 10^{4}$ M, more preferably less than $1 \times 10^{-5}$ M.

The IgG-binding peptide of the present invention binds to the Fc domain of IgG. As shown in Examples mentioned later, the IgG-binding peptide of the present invention may be placed, at the Xaa1, in proximity to a particular region of IgG Fc, i.e., a Lys248 residue (hereinafter, also simply referred to as "Lys248"; which corresponds to the 18th residue of human IgG CH2 (SEQ ID NO: 8)).

The peptide of the present invention may be produced by, for example, a conventional peptide synthesis method such as a liquid-phase synthesis method or a solid-phase synthesis method, or peptide synthesis using an automatic peptide synthesizer (Kelley et al., Genetics Engineering Principles and Methods, Setlow, J. K. eds., Plenum Press NY. (1990) Vol. 12, p. 1-19; S tewart et al., Solid-Phase Peptide Synthesis (1989) W.H. Freeman Co.; Houghten, Proc. Natl. Acad. Sci. USA (1985) 82: p. 5132; and "Shin Seikagaku Jikken Koza (New Biochemical Experimental Lecture Series in English) 1, Protein IV" (1992), ed. by The Japanese Biochemical Society, Tokyo Kagaku Dojin Co., Ltd.). Alternatively, the peptide may be produced by, for example, a gene recombination method using a nucleic acid encoding the peptide of the present invention, or a phage display method. For example, the peptide of interest may be produced by incorporating DNA encoding the amino acid sequence of the peptide of the present invention into an expression vector, transferring it to host cells, and then culturing them. The produced peptide may be recovered or purified by a routine method, for example, chromatography such as gel filtration chromatography, ion-exchange column chromatography, affinity chromatography, reverse-phase column chromatography, or HPLC, ammonium sulfate fractionation, ultrafiltration, and/or immunoadsorption.

In the peptide synthesis, for example, amino acids are prepared such that the functional groups, except for an α-amino group and an α-carboxyl group for use in bonds, of these amino acids (regardless of being natural or non-natural) are protected. Peptide bond formation reaction is performed between the α-amino group of one amino acid and the α-carboxyl group of another. Usually, the carboxyl group of an amino acid residue positioned at the C terminus of the peptide is immobilized onto a solid phase via an appropriate spacer or linker. The protective group at the amino terminus of the dipeptide thus obtained is selectively removed, and a peptide bond is formed between the deprotected amino group and the α-carboxyl group of the subsequent amino acid. A peptide having protected side groups is produced by continuously performing such operation. Finally, all of the protective groups are removed, and the peptide is separated from the solid phase. Details about the type of the protective group, the protection method, and the peptide bond method are described in the literatures described above.

The production by the gene recombination method may be performed by a method which involves, for example, inserting DNA encoding the peptide of the present invention into an appropriate expression vector, transferring the vector to appropriate host cells, culturing the cells, and recovering the peptide of interest from the inside of the cells or the extracellular fluid. The vector is not limited and is, for example, a vector such as a plasmid, a phage, a cosmid, a phagemid, or a virus.

Examples of the plasmid vector include, but are not limited to, E. coli-derived plasmids (such as pET22b(+), pBR322, pBR325, pUC118, pUC119, pUC18, pUC19, and pBluescript), Bacillus subtilis-derived plasmids (such as pUB110 and pTP5), and yeast-derived plasmids (such as YEp13 and YCp50).

Examples of the phage vector include, but are not limited to, T7 phage display vectors (such as T7Select 10-3b, T7Select 1-1b, T7Select 1-2a, T7Select 1-2b, T7Select 1-2c (Novagen)), and λ phage vectors (such as Charon 4A, Charon 21A, EMBL3, EMBL4, λgt10, λgt11, λZAP, λZAPII). Examples of the virus vector include, but are not limited to, animal viruses such as retrovirus, adenovirus, adeno-associated virus, vaccinia virus, and hemagglutinating virus of Japan, and insect viruses such as baculovirus. Examples of the cosmid vector include, but are not limited to, Lorist 6, Charomid 9-20, and Charomid 9-42.

The phagemid vector is not limited, and, for example, pSKAN, pBluescript, pBK, and pComb3H are known. The vector may contain a control sequence that permits expression of the DNA of interest, a selective marker for the selection of a vector containing the DNA of interest, a multicloning site for insertion of the DNA of interest, and the like. Such a control sequence includes, for example, a promoter, an enhancer, a terminator, a S-D sequence or a ribosomal binding site, a replication origin, and a poly-A site. For example, an ampicillin resistance gene, a neomycin resistance gene, a kanamycin resistance gene, or a dihydrofolate reductase gene can be used as the selective marker. The host cells to which the vector is transferred are, for example, cells of a bacterium such as E. coli or Bacillus subtilis, yeast cells, insect cells, animal cells (such as mammalian cells), or plant cells. The transformation or transfection of these cells includes, for example, a calcium phosphate method, electroporation, a lipofection method, a particle gun method, and a PEG method. The culture of the transformed cells is performed according to an ordinary method for use in the culture of host organisms. For example, a culture solution for a microbe such as E. coli or yeast cells contains a carbon source, a nitrogen source, and inorganic salts, etc. utilizable by the host microbe.

For facilitating recovering the peptide of the present invention, the peptide produced by expression is preferably secreted into the outside of the cells. This can be performed by linking DNA encoding a peptide sequence that permits secretion of the peptide from the cells, to the 5' end of DNA encoding the peptide of interest. The fusion peptide transferred to the cell membrane is cleaved by signal peptidase so that the peptide of interest is secreted and released into the medium. Alternatively, the peptide of interest accumulated in the cells may be recovered. In this case, the cells are disrupted physically or chemically, and the peptide of interest is recovered by use of a protein purification technique.

When the IgG-binding peptide of the present invention is fused with another protein, the IgG-binding peptide and another protein may be separately prepared and then fused using a linker, if necessary, or may be prepared as a fusion protein with an optionally added appropriate linker by a gene recombination method. In this case, the fusion protein is preferably prepared so as not to impair the binding activity of the IgG-binding peptide of the present invention against IgG.

<Modified IgG-Binding Peptide>

In one aspect, the IgG-binding peptide in the present invention is preferably modified with a crosslinking agent.

As described above, the IgG-binding peptide of the present invention may be close to a specific region of IgG Fc, that is, Lys248 according to Eu numbering in human IgG Fc, in the above Xaa1 or Xaa4, as shown in the Examples described later. Therefore, crosslinked structure between Xaa1 or Xaa4 of the IgG-binding peptide (or when Xaa4 is absent, the N-terminal amino acid) and Lys248 of IgG Fc may be site-specifically formed by modifying Xaa1 or Xaa4 of the IgG-binding peptide of the present invention (or when Xaa4 is absent, the N-terminal amino acid such as phenylalanine at position 1) with a crosslinking agent and crosslinking it with IgG. Therefore, various compounds may be introduced into IgG in a specific and simple manner by modifying the IgG-binding peptide of the present invention with various compounds, modifying Xaa1 or Xaa4 (or when Xaa4 is absent, the N-terminal amino acid) with a crosslinking agent, and crosslinking it with IgG. In addition, according to the present invention, since a compound may be introduced via an IgG-binding peptide, compounds having various structures may be introduced into IgG without side reactions. Furthermore, the method of the present invention has the advantage that the yield of the obtained product is high and that the possibility of reducing the function of the antibody is low since the antibody itself is not altered.

The IgG-binding peptide of the present invention may also be used for IgG from animals other than humans, preferably mammals, for example, rats, mice, and rabbits. In this case, the site in IgG to which the IgG-binding peptide of the present invention binds may be easily determined by those skilled in the art who have read the present specification by, for example, aligning the sequence of human IgG with the sequence of IgG from other animals.

In the present invention, the "crosslinking agent" refers to a chemical substance for linking the IgG-binding peptide of the present invention and IgG Fc by a covalent bond. The crosslinking agent of the present invention can be appropriately selected by those skilled in the art, and can be a compound having at least two sites capable of binding to the desired amino acid, for example, regarding Xaa1, a lysine residue, an ornithine residue, a cysteine residue, an aspartic acid residue, a glutamic acid residue, a 2-aminosuberic acid residue, a diaminopropionic acid residue or the like, regarding Xaa4, a glycine residue, an alanine residue, a valine residue, a leucine residue, an isoleucine residue, a methionine residue, a proline residue, a phenylalanine residue, a tryptophan residue, a lysine residue, an ornithine residue, a cysteine residue, an aspartic acid residue, a glutamic acid residue, a β-alanine residue, a 2-aminosuberic acid residue, a diaminopropionic acid residue, or $NH_2$—(PEG)n-CO (n=1 to 50, 1 to 20, 1 to 10, and preferably n=1 to 7). Examples thereof include, but are not limited to, crosslinking agents preferably containing two or more succinimidyl groups such as DSG (disuccinimidyl glutarate) and DSS (disuccinimidyl suberate), crosslinking agents preferably containing two or more imido acid moieties such as DMA (dimethyl adipimidate.2HCl, dimethyl adipimidate dihydrochloride), DMP (dimethyl pimelimidate.2HCl, dimethyl pimelimidate dihydrochloride) and DMS (dimethyl suberimidate.2HCl, dimethyl suberimidate dihydrochloride), and crosslinking agents having an SS bond such as DTBP (dimethyl 3,3'-dithiobispropionimidate.2HCl, dimethyl 3,3'-dithiobispropionimidate dihydrochloride) and DSP (dithiobis(succinimidyl propionate)).

The IgG-binding peptide of the present invention may be modified with another functional ligand, for example, a labeling substance and/or another drug (for example, antibodies such as IgA or VHH). In one embodiment, the IgG-binding peptide of the present invention has the arginine residue at position 7 in SEQ ID NO: 1 or the arginine residue at position 8 in SEQ ID NO: 2 substituted with a lysine residue, or further contains a lysine residue at the C-terminus of SEQ ID NO: 1 or SEQ ID NO: 2, and a functional ligand, for example, a labeling substance and/or another drug are linked to the IgG-binding peptide at the substituted lysine residue or the C-terminal lysine residue. The labeling substance and/or another drug may be directly linked to the IgG-binding peptide, or may be linked by attaching a molecule such as PEG (polyethylene glycol). The number of PEG molecules when attaching PEG is not particularly limited, and for example, 1 to 50 molecules, 1 to 20 molecules, 2 to 10 molecules, 2 to 6 molecules, or 4 molecules of PEG can be added.

The linking of the IgG-binding peptide to the additional functional substance may be performed by a method known to those skilled in the art, for example, the reaction between an azide group and dibenzocyclooctyne or the reaction between a maleimide group and a sulfhydryl group. The IgG can be detected or quantified via the labeling agent, when the IgG-binding peptide of the present invention labeled with a labeling agent forms a conjugate with IgG. Examples of the labeling agent include, but are not limited to, fluorescent dyes, chemiluminescent dyes, radioisotopes (such as radioactive iodine or a chelate complex of a radioisotope metal ion, for example, a chelate complex of DOTA or desferoxamine), biotin, fluorescent proteins such as GFP (green fluorescent protein), luminescent proteins, and enzymes such as peroxidase. As a preferred example, the labeling agent is a fluorescent dye including fluorescein and fluorescein derivatives such as FITC, rhodamine and rhodamine derivatives such as tetramethylrhodamine, and Texas Red. In the case of modifying the peptide of the present invention with an additional drug, examples of the drug include, but are not limited to: anticancer agents such as auristatin (such as auristatin E), maytansine, emtansine, doxorubicin, bleomycin, and their derivatives; and targeting agents such as drugs that permit transfer to the central nerve through binding to a receptor on the blood-brain barrier, and drugs that permit transfer of an antibody into cancer cells or the like through binding to the cells. When the IgG-binding peptide of the present invention is linked to a drug, the peptide may forms a conjugate with IgG, for example, for use as an antibody drug to enhance therapeutic effects on a disease.

The IgG-binding peptide modified with a cross-linking agent according to the present invention can be produced, for example, by reacting the IgG-binding peptide obtained according to the method described in the preceding section <IgG-binding peptide> with the cross-linking agent. In this case, the side chain of the amino acid residue Xaa1 or Xaa4 in the IgG-binding peptide needs to be specifically modified. This may be achieved by selecting, for example, the type of the Xaa1 or Xaa4 and its combination with the cross-linking agent. For example, the cross-linking agent containing succinimidyl groups, such as DSS or DSG, reacts with amine (c amino group) at the side chain of a lysine residue and primary amine (a amino group) present at the N terminus of a polypeptide. Therefore, the N terminus of the IgG-binding peptide may be blocked, and then, the IgG-binding peptide may be reacted with DSS or DSG to specifically modify only the side chain of the lysine residue with the DSS or the DSG. Such a combination of the amino acid residue with the cross-linking agent may be appropriately selected by those skilled in the art. Further, when using DSS or DSG, a amino group may be specifically modified by not modifying primary amine (a amino group) present at the N terminus of a polypeptide comprising no lysine residue.

The IgG-binding peptide modified with a cross-linking agent according to the present invention may also be produced by peptide synthesis using, for example, an amino acid residue modified with the cross-linking agent. Likewise, in the case of modifying the IgG-binding peptide with a labeling agent and/or an additional drug, the IgG-binding peptide modified with the labeling agent and/or the additional drug may be prepared by peptide synthesis using an amino acid residue thus modified.

<Cross-Linking Reaction>

In one aspect, the present invention relates to a method for producing a conjugate of an IgG-binding peptide and IgG, comprising a step of mixing the IgG-binding peptide modified with a cross-linking agent according to the present invention with the IgG. This step can cause cross-linking reaction between the IgG-binding peptide modified with a cross-linking agent and the IgG. The cross-linking reaction may occur site-specifically, particularly, between the amino acid residue Xaa1 or Xaa4 of the IgG-binding peptide and Lys248 of IgG Fc.

Conditions for the mixing step are not particularly limited as long as the conditions result in the cross-linking reaction between the IgG-binding peptide of the present invention and the IgG. For example, the IgG-binding peptide of the present invention and the IgG may be reacted by mixing at room temperature (such as approximately 15° C. to 30° C.) in an appropriate buffer. The mixing step may be performed by the addition of a catalyst that accelerates the cross-linking reaction in an appropriate amount, if necessary.

The reaction conditions may be adjusted to increase the binding activity between the IgG-binding peptide and IgG. For example, protein A, which is derived from the Z34C peptide, is known to increase the binding activity to human IgG3 at pH 8 or more, and is also known to increase the binding activity to mouse IgG1 by increasing the salt concentration such as NaCl. With reference to such knowledge, the conditions for the crosslinking reaction of the present invention may be set.

The conditions for the reaction of the IgG-binding peptide with IgG can be appropriately determined in consideration of the types of IgG-binding peptides, IgG, and the like, and may be, but are not limited to, pH 4.5 to 6.5 (for example, pH 5.0 to 6.0, pH 5.2 to 5.8, pH 5.4 to 5.6, or pH about 5.5), or pH 6.5 to 8.5 (for example, pH 6.9 to 7.9, pH 7.2 to 7.7, pH 7.3 to 7.5, or pH about 7.4).

The mixing ratio between the IgG-binding peptide of the present invention and the IgG in the mixing step is not particularly limited. The molar ratio between the IgG-binding peptide of the present invention and the IgG may be set to, for example, 1:1 to 20:1, preferably 2:1 to 20:1 or 5:1 to 10:1.

The mixing time (reaction time) in the mixing step is not limited as long as the mixing time results in the cross-linking reaction between the IgG-binding peptide of the present invention and the IgG. The mixing time can be, for example, 1 minute to 5 hours, preferably 10 minutes to 2 hours or 15 minutes to 1 hour.

The method for producing a conjugate of the IgG-binding peptide of the present invention and IgG may further comprise, if necessary, the step of purifying the conjugate by separating impurities, for example, unreacted IgG-binding peptides and IgG, and reagents, from the mixture after the step described above. This step can be performed by a method known in the art, for example, chromatography such as gel filtration chromatography, ion-exchange column chromatography, affinity chromatography, reverse-phase column chromatography, or HPLC.

<Conjugate>

In one aspect, the present invention relates to a cross-linked conjugate of the IgG-binding peptide of the present invention and IgG. The conjugate may be formed through the cross-linking reaction described above. Accordingly, the present invention preferably relates to a conjugate of the IgG-binding peptide and IgG, wherein the amino acid residue Xaa1 or Xaa4 of the IgG-binding peptide is site-specifically linked to Lys248 of IgG Fc via a cross-linking agent.

Since the conjugate of the present invention is formed through site-specific cross-linking reaction, the cross-linking reaction may not negatively influence the activity of IgG. Also, new functionality may be added to IgG by linking the modified IgG-binding peptide to the IgG. For example, the IgG can be detected or quantified via the labeling agent, by linking the IgG-binding peptide modified with a labeling agent to IgG. Examples of the labeling agent are as described above. Therefore, the description thereof is omitted here. For example, the IgG-binding peptide modified with a drug is bound to an antibody drug IgG. As a result, the therapeutic effects of the IgG on a disease can be enhanced. Examples of the drug are as described above, and thus the description thereof is omitted here.

<Pharmaceutical Composition or Diagnostic Agent>

In one aspect, the present invention relates to a pharmaceutical composition or a diagnostic agent comprising the IgG-binding peptide, the IgG-binding peptide modified with a cross-linking agent, or the conjugate of the IgG-binding peptide modified with a cross-linking agent and IgG. When the IgG-binding peptide is contained in the pharmaceutical composition, the peptide is preferably modified with, for example, the drug described above. When the IgG-binding peptide is contained in the diagnostic agent, the peptide is preferably modified with, for example, the labeling agent described above.

Examples of the disease targeted by the pharmaceutical composition and the diagnostic agent of the present invention include, but are not limited to, diseases or disorders targetable by antibodies, preferably cancers, inflammatory diseases, infections, and neurodegenerative diseases.

The pharmaceutical composition of the present invention may be administered by oral administration or parenteral administration (such as intravenous injection, intramuscular injection, subcutaneous administration, intraperitoneal administration, rectal administration, or transmucosal administration). The pharmaceutical composition of the present invention can be in an appropriate dosage form depending on the administration route. Specifically, the pharmaceutical composition of the present invention can be prepared as various forms of preparations including granules, tablets, pills, capsules, syrups, emulsions, suspensions, injections for intravenous injection, intraarterial injection, or intramuscular injection, drops, agents for external use, and suppositories. The administration method and the dosage form can be appropriately selected by those skilled in the art depending on the sex, age, body weight, symptoms, etc. of a patient.

The pharmaceutical composition of the present invention can be formulated according to a routine method (see, for example, Remington's Pharmaceutical Science, latest edition, Mark Publishing Company, Easton, USA) and may also contain a pharmaceutically acceptable carrier or additive.

Examples of the carrier and the pharmaceutical additive that may be contained in the pharmaceutical composition of the present invention include water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerin, glycerin, propylene glycol, Vaseline, paraffin, stearyl alcohol, stearic acid, human serum albumin (HSA), mannitol, sorbitol, lactose, and surfactants acceptable as pharmaceutical additives.

Actual additives are selected alone or in appropriate combination from among those described above depending on the dosage form of the pharmaceutical composition of the present invention, though the additives are not limited to them. For example, for use as a preparation for injection, the IgG-binding protein of the present invention or the conjugate of the IgG-binding protein and IgG is dissolved in a solution, for example, saline, a buffer solution, or a glucose solution, to which an agent preventing adsorption onto containers, for example, Tween 80, Tween 20, gelatin, or human serum albumin, is added. The resulting mixture may be used. Alternatively, a freeze-dried product may be used for a dosage form that is reconstituted by thawing before use. For example, a sugar alcohol and/or a saccharide, such as mannitol or glucose, may be used as a stabilizer for the freeze drying.

The effective dose and dosing interval of the pharmaceutical composition of the present invention can be appropriately selected depending on the sex, age, body weight, and symptoms, etc. of a patient.

The time when the pharmaceutical composition of the present invention is administered may be not limited to either before or after occurrence of clinical symptoms of the disease, and may be preventive administration or therapeutic administration.

EXAMPLES (Materials and Methods)
Antibodies

Trasutumab (Human IgG1) was purchased from Chugai Pharmaceutical Co., Ltd., and Human IgG2 kappa Isotype Control, Human IgG3 kappa Isotype Control, Human IgG4 kappa Isotype Control, Mouse IgG1 kappa Isotype Control, Mouse IgG2b kappa Isotype Control and Mouse IgG3 kappa Isotype Control were purchased from Crown Bioscience Inc. Moreover, Rabbit IgG Isotype Control was obtained from Thermo fisher, Rat IgG1 Isotype Control and Rat IgG2b Isotype Control from R&D Systems, Inc., and Rat IgG2c Isotype Control Antibody from LifeSpan BioSciences. The powder of each antibody was diluted to 2.0 mg/mL with 0.5 M NaCl and stored frozen until use.
Preparation of the Z34C Peptide Variant The Z34C peptide variant was prepared by solid phase synthesis according to the F-moc method. 5.5 mg (1.29 μmol) of Z34C-derived peptide after synthesis was dissolved in 10 μL of dimethyl sulfoxide (DMSO) (Wako), 190 μL of 0.1 M NaHCO$_3$ aqueous solution was added thereto, and it was allowed to stand overnight at room temperature to form an intramolecular SS bond. Then, the sample was diluted with 3 mL of 1% acetonitrile containing 0.1% TFA, and the whole amount was applied to a preparative chromatograph LC-forte/R (YMC). Elution was performed with a gradient of 10-60% acetonitrile/water containing 0.1% TFA, then, the organic solvent was removed under reduced pressure, followed by freeze-drying.
Molecular Weight Analysis by LC-MS for Product Identification To confirm the structure of the reaction product, 0.1 μL of the reaction solution was diluted 4000 times with a 0.1% formic acid aqueous solution, 18 μL of which was applied on a LCMS-8030 (Shimadzu) connected to a kinetex (registered trademark) LC column (1.7 μm, EVO C18 100 angstroms, Phenomenex). Gradient elution was performed with 10-50% acetonitrile/water containing 0.1% formic acid at a flow rate of 0.2 mL/min, and the mass of the resulting peak was confirmed and analyzed.
Molecular Structure Modeling The Z34C variant modeling and modification site design were performed using the molecular structure calculation software MOE (The Molecular Operating Environment, CCG). Based on the crystal structure of human IgG1-Fc and Z34C peptide (PDB ID: 1OQO), the variable sites on the peptide were searched, and modeling was performed using Protein Builder tools.
Modification of Z34C Peptide Variant with DSG The modification of the N-terminal α-amino group or the ε-amino group of Lys of the Z34C peptide variant with DSG (N,N'-Disuccinimidyl glutarate) was performed by the following method. After dissolving 1 to 2 mg of the peptide in 40 μL of DMSO, 0.1% pyridine was added, 20 μL of 500 mM DSG dissolved in acetonitrile was added, and allowed to react at 50° C. for 4.5 hours. The reaction product was diluted with 3 mL of 1% acetonitrile containing 0.1% TFA, and the whole amount was applied to a preparative chromatograph LC-forte/R (YMC). Elution was performed with a gradient of 10-60% acetonitrile/water containing 0.1% TFA, then, the organic solvent was removed under reduced pressure, followed by freeze-drying to obtain a succinimidyl glutarate (SG)-modified Z34C peptide variant.
Peptide Affinity Analysis The Z34C peptide variant affinity analysis was performed on BIAcore T-200 (GE-Healthcare) at 25° C. That is, Trastuzumab (human IgG1 antibody) or other antibodies were immobilized in an amount of approximately 2000 in terms of RU value, on a CM5 sensor chip according to the protocol for amine coupling. Sensorgrams (association time: 180 sec, dissociation time: 600 sec) were obtained by injecting a total of 7 different concentrations of peptides from 1 μM to 0.015 μM as analytes in HBS-EP buffer solution at a flow rate of 50 μL/min, and the dissociation constant (Kd) was calculated from the equilibrium value analysis using the bundled BIA evaluation software.
Labeling of Antibodies with SG-Modified Z34C Variant Peptide Reagent and Confirmation of
Labeling by SDS-PAGE 1.33 μL (10-fold molar equivalents, 2 nmol) of the SG-modified Z34C peptide variant peptide dissolved in DMSO to be 1.5 mM was added to 3.0 μg (0.2 nmol) of each antibody dissolved in 14 μL of 10 mM acetate buffer solution (pH 5.5), and left at room temperature for 30 minutes. To 14.4 μL of this sample, 0.6 μL of 2-mercaptoethanol (Wako) and 5 μL of SDS-PAGE sample buffer (4×) were added to make a total volume of 20 μL (3% 2-mercaptoethanol). After reduction by heating at 95° C. for 10 minutes, electrophoresis was performed with Super Sep™ Ace (5-20%, 13 well, Wako 197-15011) at 200 V, 20 mA for about 90 minutes. The resulting gel protein was detected by performing CBB (Coomassie Brilliant Blue) staining.
ELISA Mouse IgG1, IgG2b, and human IgG3 (all recognize hen egg white lysozyme as an antigen) and Trastuzumab (human IgG1), which is an anti-HER2 antibody, were dissolved in 10 mM acetate buffer solution (pH 5.5) (final concentration 2.5 μM), 10-fold equivalent amount of peptide reagents αZ34C 7K and εZ34C 7K dissolved in DMSO were added and allowed to react at room temperature for 30 minutes. The reaction was stopped by adding 1/10 volume of 1M Tris-HCl (pH 8.0), diluted 5000 times with PBS containing 0.5% BSA, and then used for ELISA. The antigen, lysozyme was diluted with PBS to 200 µg/L, 100 µg/L, and 50 µg/L, and each well was coated (2 hours). Next, it was blocked with a PBS solution containing 0.5% BSA, and after washing, 50 µL of diluted antibody solution was added to each well and allowed to react for 1 hour. After washing, SA-HRP (Vector) diluted 5000 times with a PBS solution containing 0.5% BSA was added to the wells, and after the reaction, the wells were washed, and TMB reagent was added to develop color.

Results

Example 1: Preparation of Substituted Peptide Based on Z34C Peptide

Figure 2:
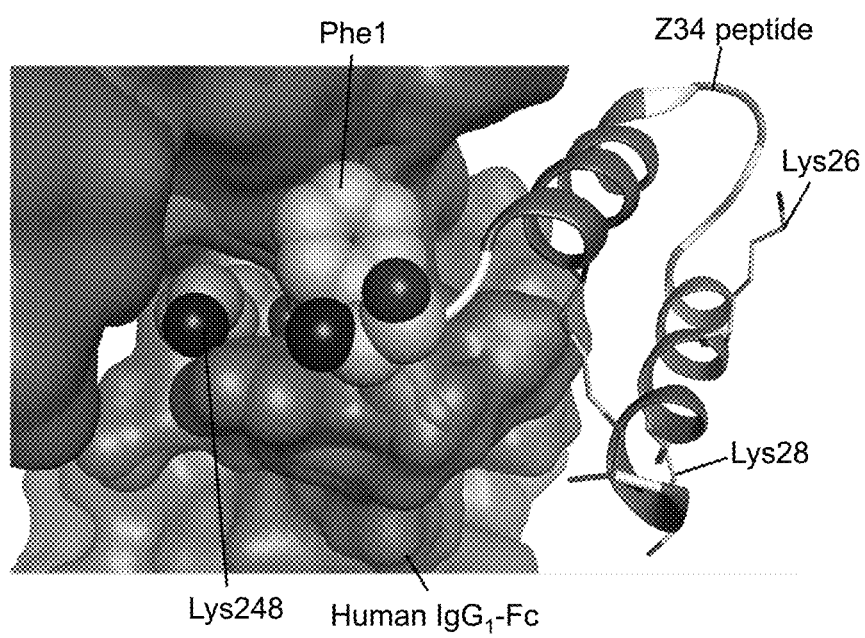
FIG. 2 shows (A) a model structure for the binding of Z34C peptide and human IgG, and (B) a model structure for the binding of Z34C-derived peptide (εz34C) and human IgG.
Figure 2:
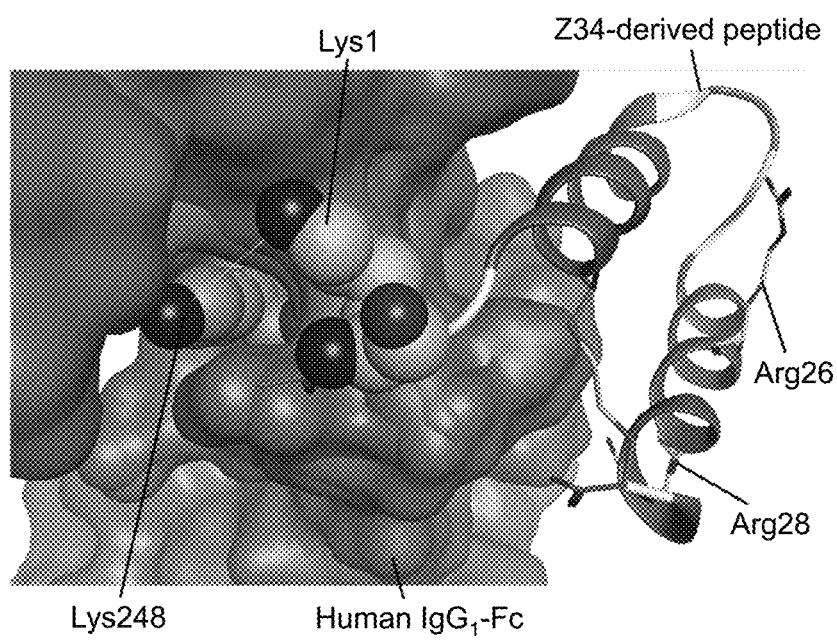

When searching the amino acid residues on Z34C peptide proximal to Lys248 in human IgG1-Fc based on the X-ray crystal structure of human IgG1-Fc and Z34C peptide (PDB ID: 1OQO, 10), it was found that the side chain of N-terminal phenylalanine was closest to Lys248 in IgG1-Fc (FIG. 2A). Next, the N-terminal phenylalanine of the Z34C peptide was substituted with lysine, and when the distance between Lys248 of Fc and the ε-amino group of Lys1 of the substituted Z34C peptide was measured, it was found that the closest distance can be up to 6.57 angstroms (FIG. 2B). Therefore, it was attempted to confirm whether or not the crosslinking between these two amino groups was actually possible, by synthesizing a variant peptide.

First, in order to remove the amino group that may be modified by reaction with DSG, εZ34C (Z34C (F1K, K26R, K28R)) peptide was prepared, in which lysines at positions 26 and 28 of the Z34C peptide were substituted with arginine, and phenylalanine at position 1 was substituted with lysine to further modify it with SG. The amino acid sequences of the Z34C peptide and εZ34C peptide are shown in Table 1 below (provided that the N-terminus and C-terminus of each peptide were acetylated and amidated, respectively).

TABLE 1

| Peptide | Amino acid sequence | SEQ ID NO |
|---|---|---|
| Z34C | FNMQCQRRFYEALHDPNLNEEQRNAKIKSIRDDC | 3 |
| εZ34C | KNMQCQRRFYEALHDPNLNEEQRNARIRSIRDDC | 4 |

After forming the intramolecular disulfide bond of the εZ34C peptide, the affinity of the peptide with human IgG1 was evaluated by BIAcore T-200 (GE-Healthcare), and the Kd value was 17 (±1.9) nM. Since the Kd value of the original Z34C peptide is reported to be 20 nM, this revealed that the variation had almost no effect.

Next, this peptide was reacted with DSG (disuccinimidyl glutarate) to modify the side chain of lysine at position 1 with SG (succinimidyl glutarate), and the reactivity of the resulting SG-modified εZ34C peptide with each human IgG subclass was evaluated. Specifically, the results of the SDS-PAGE performed in a reduced state after reacting SG-modified εZ34C peptide with an IgG solution prepared at about 14 µm at pH 5.5 in a molar ratio of 10 times the amount are shown in FIG. 3.

Figure 3:
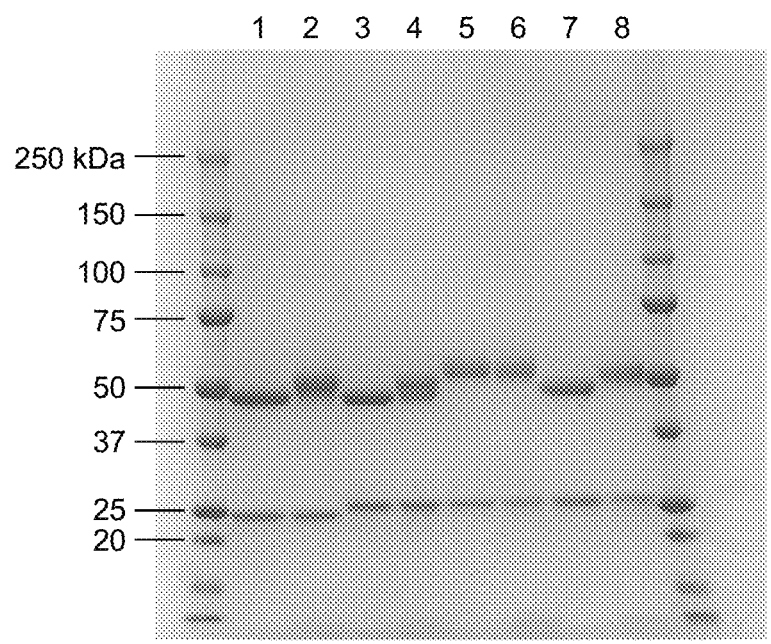
FIG. 3 shows the results of the SDS-PAGE of the reaction product of SG-modified εZ34C peptide and human IgG. The results of the SDS-PAGE are shown for human IgG1 (Trastuzumab) of lane 1, the reaction product of human IgG1 and εZ34C of lane 2, human IgG2 of lane 3, the reaction product of human IgG2 and εZ34C of lane 4, human IgG3 of lane 5, the reaction product of human IgG3 and εZ34C of lane 6, human IgG4 of lane 7, and the reaction product of human IgG4 and εZ34C of lane 8.

As shown in FIG. 3, in the reaction of SG-modified εZ34C peptide with human IgG, the position of the light chain band of IgG1-4 did not change at all, whereas an increase in molecular weight by about 3000 was observed in about half of the heavy chain bands of IgG1 (Trastuzumab), IgG2, and IgG4 (about 50 kDa). This indicates that the SG-modified εZ34C peptide is specifically added by a covalent bond to at least the heavy chain of IgG except IgG3.

Example 2: Preparation of Substituted Peptide Based on Z34C Peptide 2

A substituted peptide αZ34C peptide (Z34C (-1G, K26R, K28R)) was designed, in which one glycine is added to the N-terminus of Z34C, without substituting Phe1Lys. In the model structure of αZ34C, the distance between the α-amino group of N-terminal glycine and the ε-amino group of Lys248 in the Fc of IgG was 8.0 angstroms, suggesting that it could be sufficiently crosslinked with a crosslinking agent such as DSG.

In addition, as the biotin-labeled site of the αZ34C peptide and the εZ34C peptide prepared in Example 1, arginine at position 7 which was exposed to a solvent and whose side chain extends on the opposite side of the binding site with the antibody was converted to lysine, and the ε amino group was modified with PEG4-biotin (referred to as εZ34C 7K and αZ34C 7K, respectively). The structures of the two types of biotinylated labeled peptides are shown in Table 2 below (provided that the N-terminus and C-terminus of Z34C and εZ34C 7K were acetylated and amidated, respectively, and that the αZ34C 7K peptide was not modified at the N-terminus and only C-terminal amidation was performed).

TABLE 2

| Peptide | Amino acid sequence | SEQ ID NO |
|---|---|---|
| Z34C | FNMQCQRRFYEALHDPNLNEEQRNAKIKSIRDDC | 3 |
| αZ34C 7K | GFNMQCQKRFYEALHDPNLNEEQRNARIRSIRDDC | 5 |
| εZ34C 7K | KNMQCQKRFYEALHDPNLNEEQRNARIRSIRDDC | 6 |

SG-modification was performed on these peptides by the same method as in Example 1, and the reactivity with the antibodies was evaluated. That is, an SG group was introduced into the N-terminal α-amino group in the αZ34C 7K peptide and into the ε-amino group of Lys1 in the εZ34C 7K peptide, and the labeling ability of human, mouse, and rat antibodies was examined by SDS-PAGE.

Figure 4:
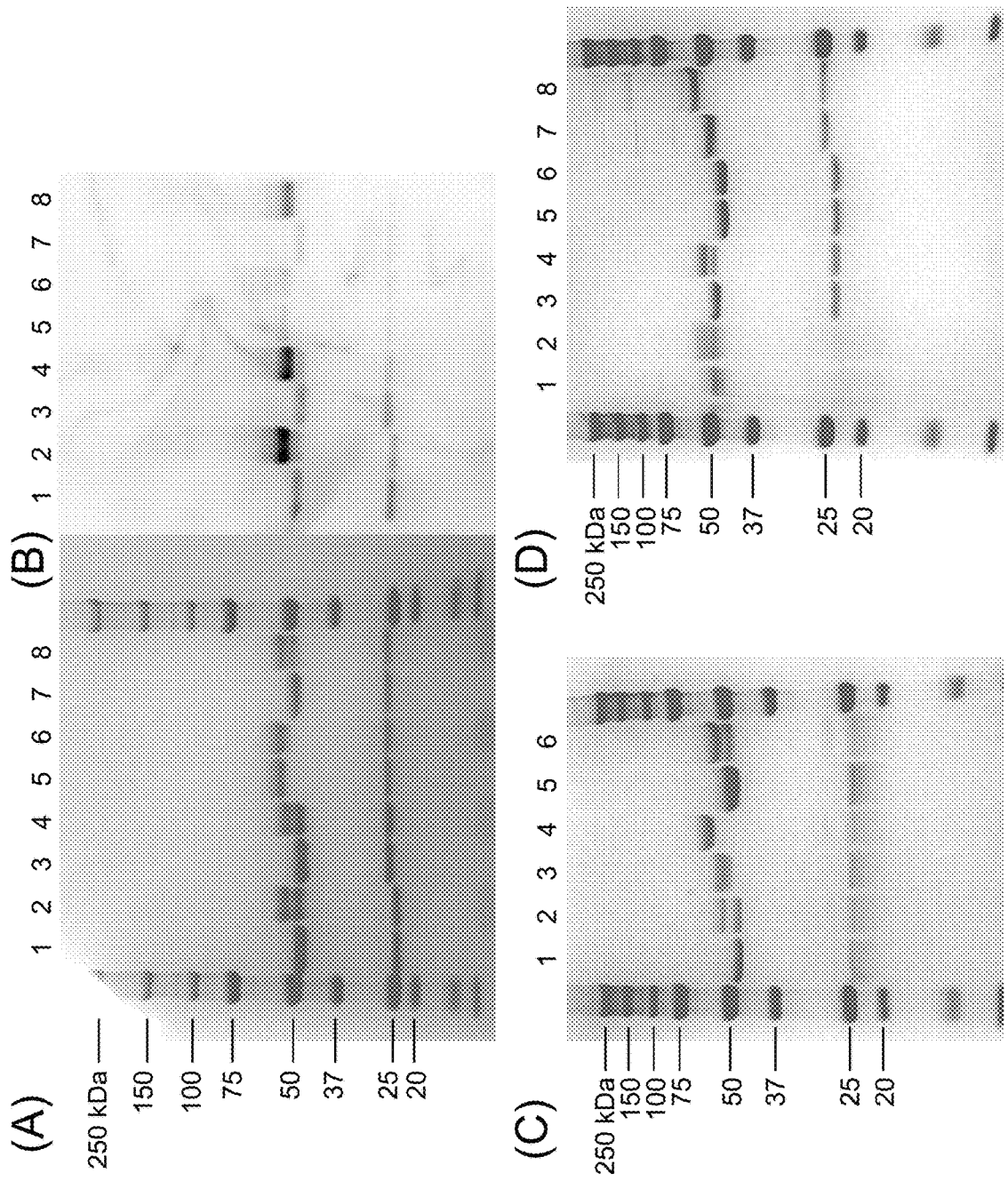
FIG. 4 shows the results of the SDS-PAGE of the reaction product of SG-modified αZ34C 7K peptide and human IgG, mouse IgG, and rabbit and rat IgG, (A, C, and D, respectively) and the results of the western blotting of the reaction product of SG-modified αZ34C 7K peptide and human IgG (B).

As shown in FIG. 4A, regarding the SG-modified αZ34C 7K peptide, an increase in molecular weight by about 3000 was clearly observed in about half of the heavy chains (band of about 50 kDa) for human IgG1, 2, and 4, as seen in FIG. 3. On the other hand, no change in molecular weight was observed in the light chains of IgG1 to 4 and the heavy chain of IgG3. To further confirm this point, when the proteins were transferred from the gel after electrophoresis to a PVDF membrane and stained using SA-HRP, only the heavy chain bands with increased molecular weight were strongly stained in human IgG1, 2 and 4 (FIG. 4B), indicating that the shifted band contained the biotinylated peptide reagent. On the other hand, a similar shift was also observed in the heavy chains of mouse IgG1, 2b, and 3 (FIG. 4B), and a shift was also observed in rabbit IgG, rat IgG1 and IgG2c (FIG. 4C), indicating that the reaction occurred. On the other hand, no band change was observed in the heavy chain of rat IgG2b (FIG. 4C).

Figure 5:
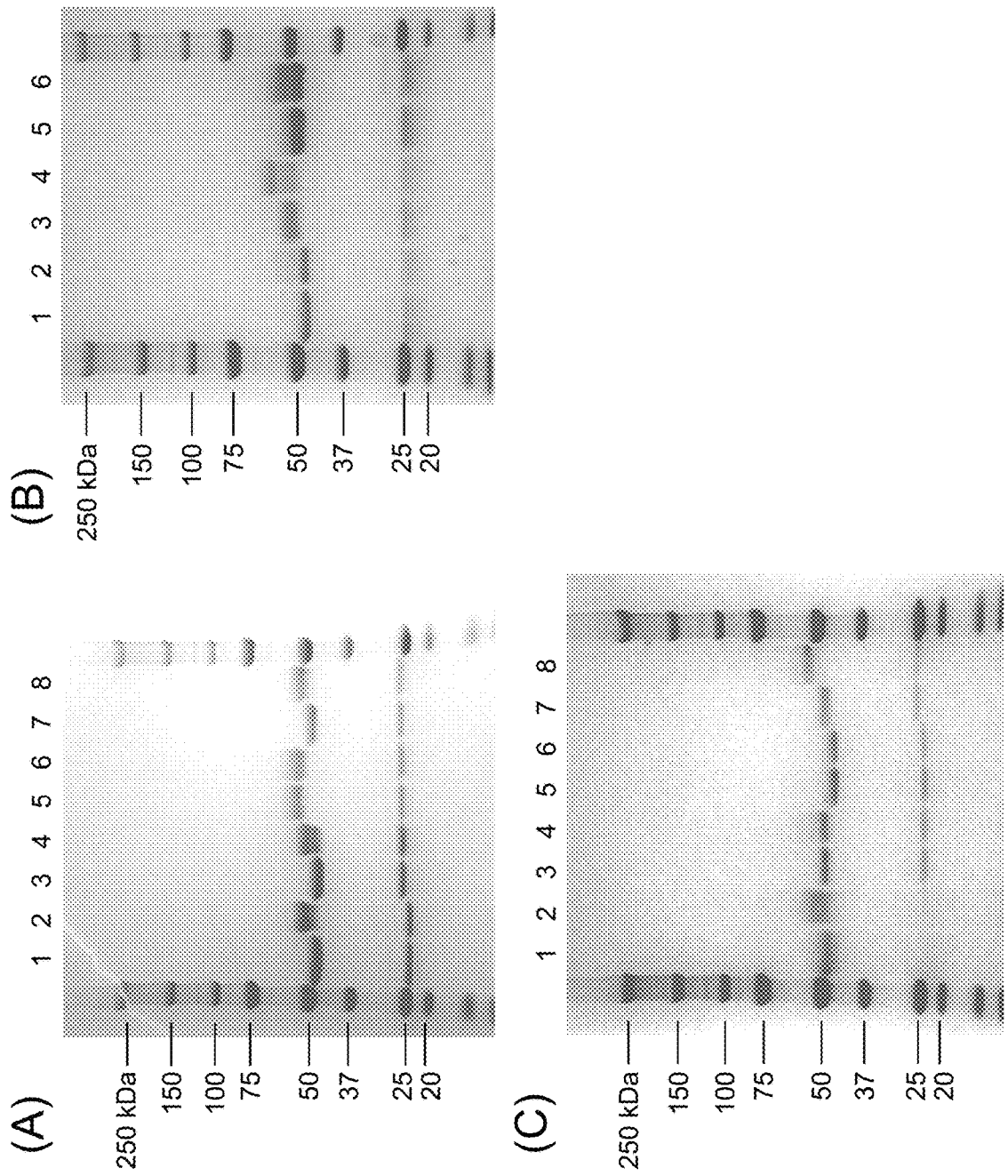
FIG. 5 shows the results of the SDS-PAGE of the reaction product of SG-modified εZ34C 7K peptide and human IgG, mouse IgG, and rabbit and rat IgG, (A, B, and C, respectively).

Similarly, the reactivity of the SG-modified εZ34C 7K peptide with human, mouse, rabbit, and rat IgG was examined. As shown in FIG. 5A, after the reaction with the peptide, the heavy chains of human IgG1, 2, and 4 obtained bands whose molecular weights were shifted by about 3000, and IgG3 did not change. Since these results are almost the same as the results of the SG-modified εZ34C in FIG. 3, it was believed that the biotinylation did not have a great effect. On the other hand, in the reaction of this peptide with mouse IgG, heavy chain bands with increased molecular weight were observed in IgG2b and IgG3 (FIG. 5B), and in the reaction with rabbit and rat IgG, heavy chain bands with increased molecular weight were observed in rabbit IgG and rat IgG2c (FIG. 5C).

In order to investigate in detail the difference in reactivity of these two types of biotinylated peptides with various IgG antibodies, the results of the calculation of the modification efficiency (Y/(X+Y)×100%) from the area of the staining histogram of the heavy chain band of the SDS-PAGE after the reaction (X) and the heavy chain band in which the peptide is bound (Y), are shown in Table 3.

TABLE 3

| | | εZ34C | εZ34C 7K | αZ34C 7K |
|---|---|---|---|---|
| Human | IgG1 | 100 | 72 | 51 |
| | IgG2 | 59 | 61 | 49 |
| | IgG3 | 0 | 0 | 0 |
| | IgG4 | 100 | 100 | 60 |
| Mouse | IgG1 | — | 30 | 41 |
| | IgG2b | — | 60 | 100 |
| | IgG3 | — | 49 | 61 |
| Rabbit | IgG | — | 60 | 40 |
| Rat | IgG1 | — | 5 | 64 |
| | IgG2b | — | 0 | 0 |
| | IgG2c | — | 100 | 100 |

It is believed that such difference in reactivity with each IgG due to the difference in the amino acid sequence of the peptide is due to the difference of affinity between the peptide and the IgG antibody and to the difference in the structure near Lys248 of IgG Fc, which is the modification target site.

Example 3: Affinity Evaluation of Biotinylated Peptide-Labeled Antibodies to Various Antibodies Next, the affinity between the used biotinylated peptides (no DSG modification) and the antibodies was evaluated. Table 4 shows the results of affinity analysis of the used peptides with various IgG antibodies using BIAcore T200. The relationship between the labeling efficiencies of the various peptides in Table 3 and the affinities in Table 4 was plotted, and there appears to be no clear correlation between the affinity and the labeling efficiency between the antibodies and peptides(data not shown).

This was presumed to be due to the fact that, although the labeling reaction requires a certain amount of affinity with the Fc of the antibody, whereas, to form a crosslinking reaction by covalent bond, structural factors are likely important, such as the structure of the crosslinking agent extending from the side chain of Lys, in particular, positional relationship between the peptide and the ε-amino group of Lys248 undergoing reaction between the NHS group present at the terminus when the peptide and Fc are bound.

TABLE 4

| | | Peptide | |
|---|---|---|---|
| | | αZ34C 7K | εZ34C 7K |
| Antibody | Human IgG1 | 33 | 27 |
| | Human IgG2 | 69 | 240 |
| | Human IgG3 | No binding | No binding |
| | Human IgG4 | 62 | 19 |
| | Mouse IgG1 | 180 | 480 |
| | Mouse IgG2b | 2700 | 7100 |
| | Mouse IgG3 | 160 | 460 |
| | Rabbit IgG | 39 | 21 |
| | Rat IgG1 | 630 | 1700 |
| | Rat IgG2b | No binding | No binding |
| | Rat IgG2c | 1900 | 3300 |

Example 4: ELISA with Biotinylated Peptide-Labeled Antibodies

Figure 6:
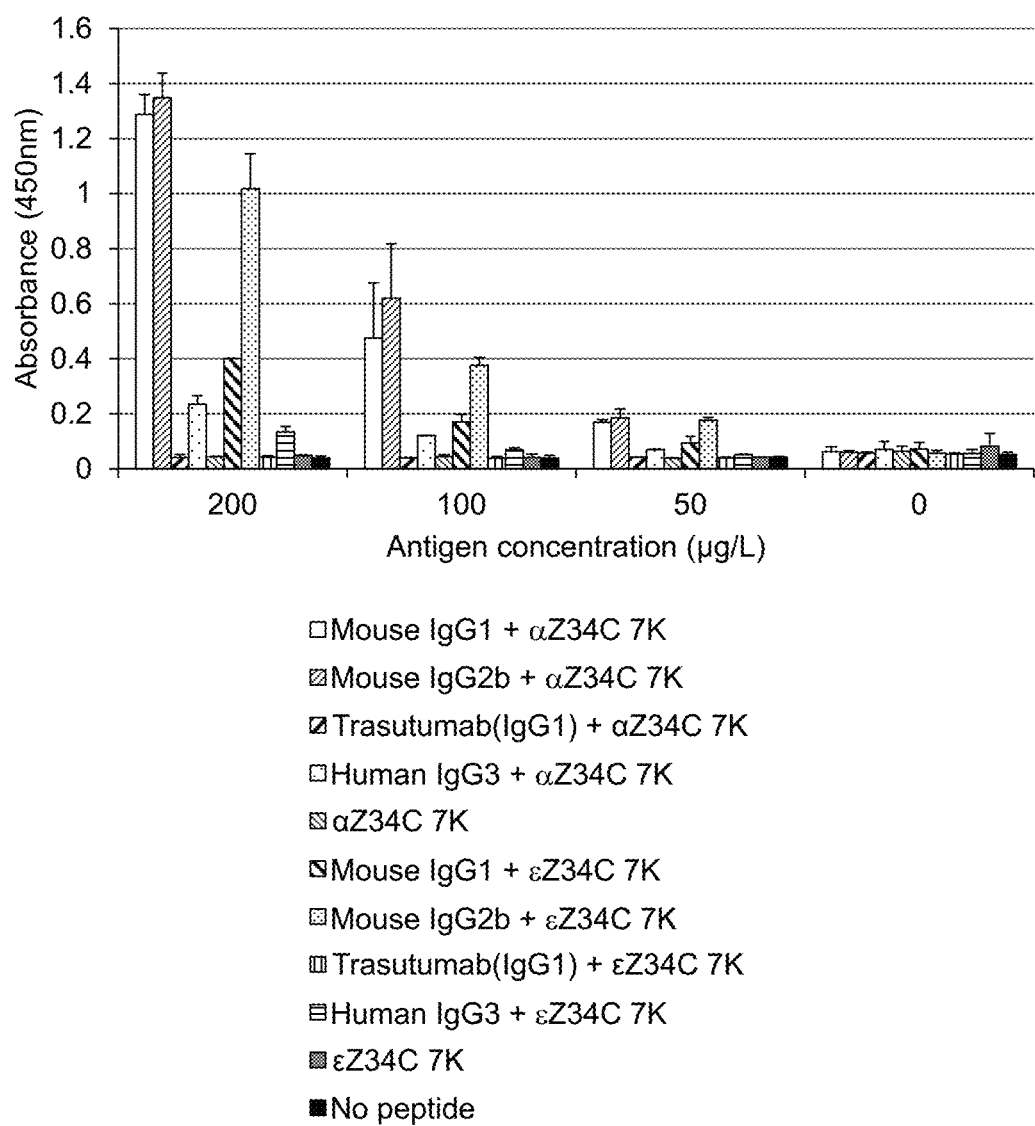
FIG. 6 shows the binding activity evaluation by ELISA of mouse IgG1, 2b and human IgG3 modified with αZ34C 7K and εZ34C 7K (the antigen of each of which is hen egg white lysozyme) and Trastuzumab (anti-HER2 human IgG1 antibody) to hen egg white lysozyme.

Mouse IgG1, IgG2b, and human IgG3 (all recognize hen egg white lysozyme as an antigen) and Trastuzumab (human IgG1), which is an anti-HER2 antibody, were reacted with αZ34C 7K and εZ34C 7K, and ELISA was performed. The results are shown in FIG. 6. As expected, mouse IgG1 and IgG2b had high binding reactivity, and binding activity was also observed for human IgG3. On the other hand, no binding activity was observed for human IgG1 which has a different target antigen (antigen is HER2).

In this way, it was shown that when the present peptide is used, the labeling reaction can be completed simply by mixing the antibody solution and the peptide solution, and the reaction solution can be used as it is in assays such as ELISA without extra purification and isolation operations.

Example 5: Reactivity of Various Peptides to IgG1

The following peptides were synthesized according to the F-moc method, and the reactivity with IgG1 at pH 5.5 was evaluated (provided that the C-termini were all amidated, only the N-terminus of εZ34C was methoxylated, and the others were aminated).

TABLE 5

| Peptide | Amino acid sequence | SEQ ID NO |
|---|---|---|
| αZ34C | GFNMQCQRRFYEALHDPNLNEEQRNARIRSIRDDC | 7 |
| εZ34C | KNMQCQRRFYEALHDPNLNEEQRNARIRSIRDDC | 4 |
| Z34C 26 28R | FNMQCQRRFYEALHDPNLNEEQRNARIRSIRDDC | 9 |
| Z33 | FNMQQQRRFYEALHDPNLNEEQRNARIRSIRDD | 10 |

1 μL of each 5 mM SG peptide dissolved in DMSO was added to 99 μL of Trastuzumab (human IgG1 antibody) dissolved in 10 mM acetate buffer solution (pH 5.5) and allowed to react at room temperature (provided that the final concentrations of Trastuzumab and the peptide reagents were 10 μM and 200 μM). After 10 minutes, 30 minutes, 1 hour, and 3 hours after the reaction, 17 μL (25 μg) was taken, 50 μL of 4×SDS sample solution containing 5% 2-mercaptoethanol (2-ME) was added and 163 μL of distilled water was added to make a total volume of 200 μL, then it was reduced by incubating at 95° C. for 10 minutes. 20 μL of the reaction solution was subjected to SDS-PAGE on a 5 to 20% gel and to CBB staining.

Figure 7:
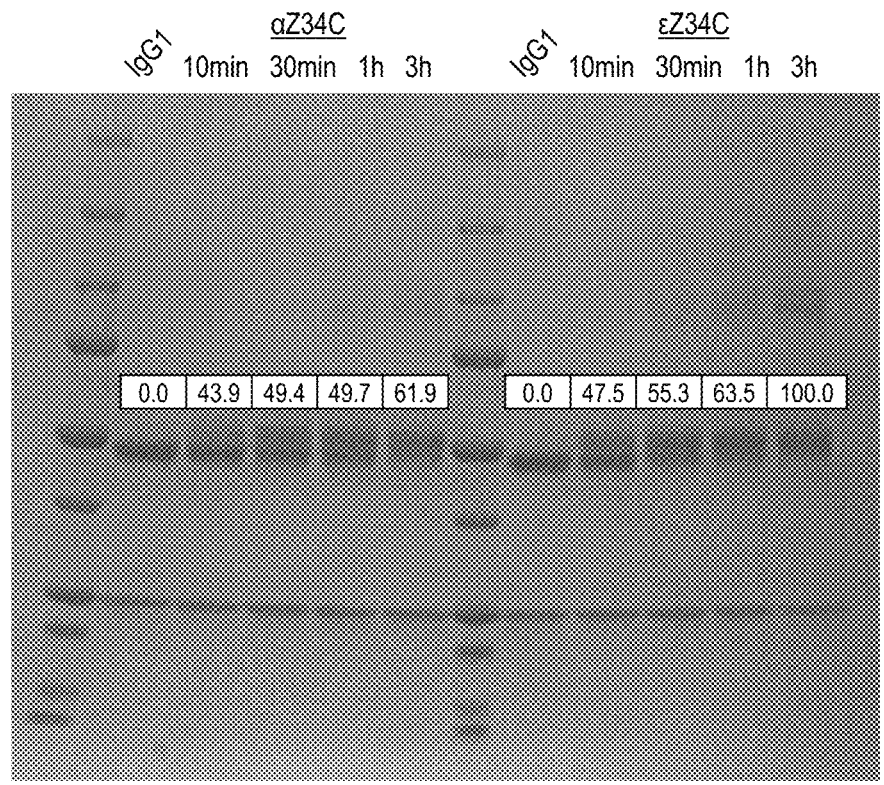
FIG. 7 shows the results of the SDS-PAGE of samples of each SG-modified polypeptide, 10 minutes, 30 minutes, 1 hour and 3 hours after their reaction with IgG1, and IgG1's modification efficiency estimated from these results.
Figure 7:
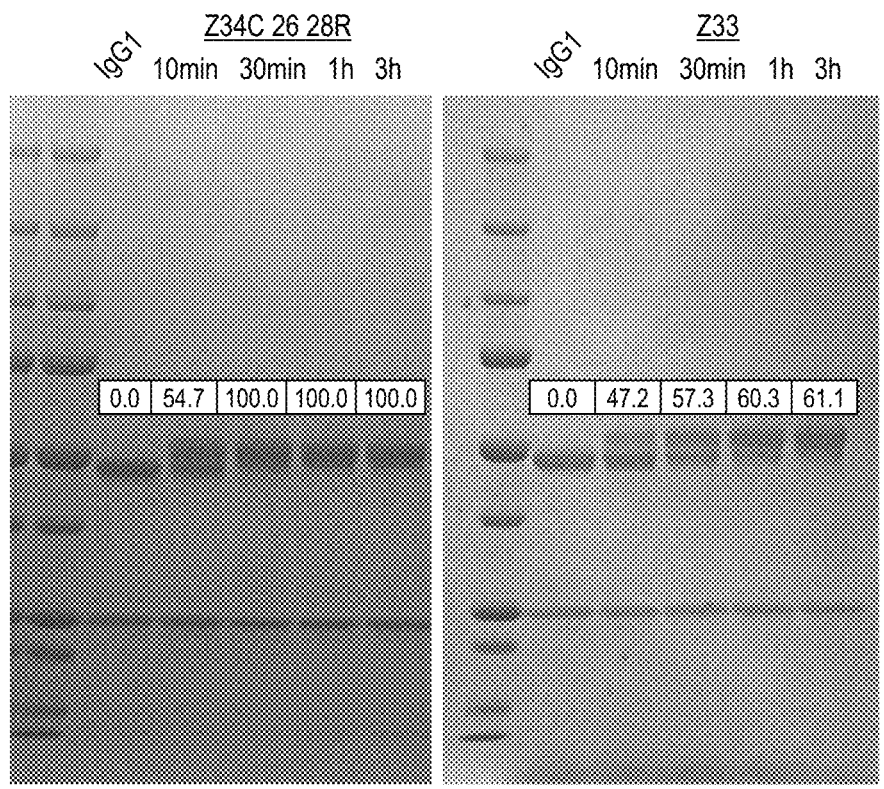

The results are shown in FIG. 7. Z34C 26 28R was the most reactive, with 100% IgG1 being modified in 30 minutes. On the other hand, the yields of αZ34C and εZ34C after 30 minutes were 49% and 55%, and the modification efficiency was about half that of Z34C 26 28R. Furthermore, although Z33 had a lower efficiency than Z34C, it was modified with almost the same efficiency as αZ34C and εZ34C.

Example 6: Examination of the Influence of pH

1 μL of the 0.5 mM SG-modified peptide reagents (three peptide reagents: Z34C 26 28R, αZ34C, and εZ34C) dissolved in DMSO was added to each IgG dissolved in 10 mM PBS (pH 7.4) (99 μL) and allowed to react at room temperature (provided that the final concentrations of the antibodies and the peptide reagents were 1 μM and 5 μM). After reacting for 3 hours, CBB staining was performed after SDS-PAGE with the same method as in Example 5.

Figure 8:
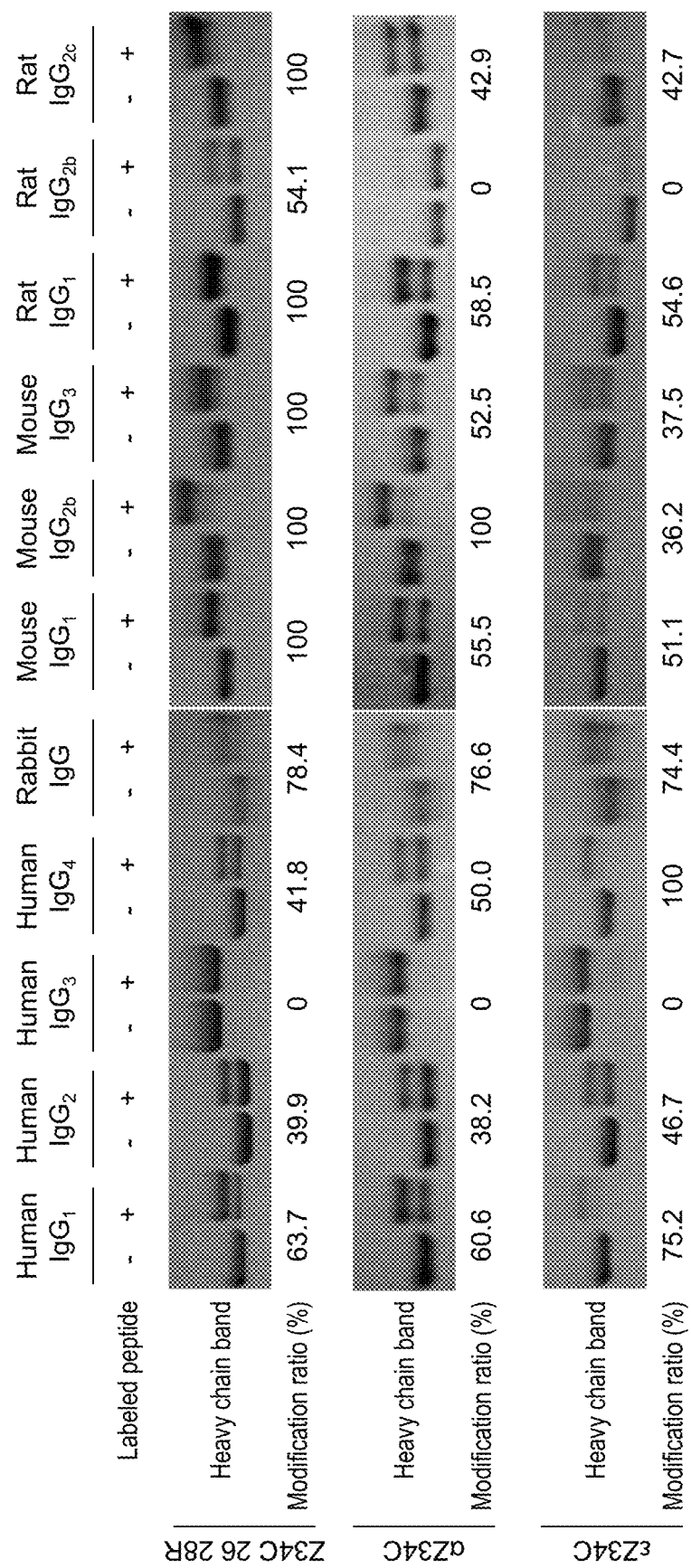
FIG. 8 shows the results of the SDS-PAGE of samples of SG-modified peptide reagents (three peptide reagents: Z34C 26 28R, αZ34C, and εZ34C), after reaction with each antibody at pH 7.4, and the modification efficiency of each antibody estimated from these results.

The results are shown in FIG. 8 and the values are summarized in Table 5 (The values in parentheses for αZ34C and εZ34C indicate the peptide modification efficiency for the antibody at pH 5.5 using αZ34C 7K and εZ34C 7K peptides in Table 3 (provided that the peptide reagents were added in a 10-fold molar ratio of the antibody)).

TABLE 6

|  |  | αZ34C | εZ34C | Z34C 26 28R |
|---|---|---|---|---|
| Human | IgG1 | 61(51) | 75(100) | 64 |
|  | IgG2 | 38(51) | 47(59) | 40 |
|  | IgG3 | 0(0) | 0(0) | 0 |
|  | IgG4 | 50(100) | 100(100) | 42 |

TABLE 6-continued

|  |  | αZ34C | εZ34C | Z34C 26 28R |
|---|---|---|---|---|
| Rabbit | IgG | 77(60) | 74 | 78 |
| Mouse | IgG1 | 56(30) | 51 | 100 |
|  | IgG2b | 100(60) | 36 | 100 |
|  | IgG3 | 53(49) | 38 | 100 |
| Rat | IgG1 | 59(5) | 55 | 100 |
|  | IgG2b | 0(0) | 0 | 54 |
|  | IgG2c | 43(100) | 43 | 100 |

At pH 5.5 and pH 7.4 with αZ34C, improved reactivity was confirmed at pH 7.4 compared with pH 5.5 (especially mouse IgG1 (30→56%), mouse IgG2b (60→100%), and rat IgG1 (5→59%)). On the other hand, the reaction yield decreased to half at pH 7.4 compared to pH 5.5, regarding human IgG4 (100→50%) and rat IgG2c (100→43%). Regarding εZ34C, no significant difference was observed for the reactivity of human IgG1-4 compared at pH 5.5 and 7.4. Regarding Z34C, comparison data with pH 5.5 is not shown, but 100% modification efficiency was achieved in mouse IgG1, IgG2b and IgG 3, and rat IgG1 and IgG 2c. Furthermore, regarding IgG2b of rat Z34C (pH 7.4), 54% of the modified form was obtained.

INDUSTRIAL APPLICABILITY

Since the IgG-binding peptide modified with the cross-linking agent of the present invention may be added to IgG in a short time and with little side reaction, various compounds may be bound to the IgG-binding peptide, allowing to modify IgG with various compounds in a specific and simple manner. Since IgG to which various compounds are added may be used as a therapeutic agent or a diagnostic agent, the industrial applicability of the present invention is high.

All publications, patents and patent applications cited in the present specification are hereby incorporated by reference in their entirety.

The invention claimed is:

1. A peptide comprising:

(SEQ ID NO: 1)
(Xaa1)NMQCQRRFYEALHDPNLNEEQRNA(Xaa2)I(Xaa3)SIRDDC, (SEQ ID NO: 2)
(Xaa4)FNMQCQRRFYEALHDPNLNEEQRNA(Xaa2)I(Xaa3)SIRDDC, (SEQ ID NO: 5)
GFNMQCQKRFYEALHDPNLNEEQRNARIRSIRDDC, (SEQ ID NO: 6)
KNMQCQKRFYEALHDPNLNEEQRNARIRSIRDDC,
or (SEQ ID NO: 11)
GKNMQCQRRFYEALHDPNLNEEQRNARIRSIRDDC;

wherein Xaa1 is selected from the group consisting of a lysine residue, an ornithine residue, a cysteine residue, an aspartic acid residue, a glutamic acid residue, a 2-aminosuberic acid residue, and a diaminopropionic acid residue;

Xaa2 and Xaa3 are each independently selected from the group consisting of an arginine residue, a histidine residue, an aspartic acid residue, a glutamic acid residue, a serine residue, a threonine residue, an asparagine residue, a glutamine residue, a tyrosine residue, and a cysteine residue; and Xaa4 is selected from the group consisting of a glycine residue, an alanine residue, a valine residue, a leucine residue, an isoleucine residue, a methionine residue, a proline residue, a phenylalanine residue, a tryptophan residue, a lysine residue, an ornithine residue, a cysteine residue, an aspartic acid residue, a glutamic acid residue, a β-alanine residue, a 2-aminosuberic acid residue, a diaminopropionic acid residue, and $NH_2$—(PEG)n-CO (n=1 to 50), or absent.

2. The peptide according to claim 1, wherein Xaa1 is selected from the group consisting of a lysine residue, an ornithine residue, a cysteine residue, and a diaminopropionic acid residue.

3. The peptide according to claim 2, wherein Xaa1 is a lysine residue.

4. The peptide according to claim 1, wherein Xaa4 is selected from the group consisting of a glycine residue, an alanine residue, a β-alanine residue, and $NH_2$-(PEG)n-CO (n=1 to 50), or absent.

5. The peptide according to claim 4, wherein Xaa4 is a glycine residue, or absent.

6. The peptide according to claim 1, wherein Xaa2 and Xaa3 are each independently selected from the group consisting of an arginine residue, a histidine residue, and a glutamic acid residue.

7. The peptide according to claim 6, wherein Xaa2 and Xaa3 are an arginine residue.

8. The peptide according to claim 1, wherein the cysteine residue at position 5 and the cysteine residue at position 34 in SEQ ID NO: 1, and the cysteine residue at position 6 and the cysteine residue at position 35 in SEQ ID NO: 2 are linked via a disulfide bond or a linker.

9. The peptide according to claim 1, comprising the amino acid sequence of:

```
                                            (SEQ ID NO: 9)
FNMQCQRRFYEALHDPNLNEEQRNARIRSIRDDC, (SEQ ID NO: 7)
GFNMQCQRRFYEALHDPNLNEEQRNARIRSIRDDC,
or (SEQ ID NO: 4)
KNMQCQRRFYEALHDPNLNEEQRNARIRSIRDDC.
```

10. The peptide according to claim 1, to which a labeling substance or a drug is bound.

11. The peptide according to claim 1, wherein the N-terminal amino acid is acetylated or aminated.

12. The peptide according to claim 1, wherein the C-terminal amino acid is amidated.

13. The binding peptide according to claim 1, wherein Xaa1 and Xaa4 are modified with a crosslinking agent, or if Xaa4 is absent, the phenylalanine at position 1 in SEQ ID NO: 2 is modified with a crosslinking agent.

14. The peptide according to claim 13, wherein the crosslinking agent is selected from the group consisting of DSG (disuccinimidyl glutarate), DSS (disuccinimidyl suberate), DMA (dimethyl adipimidate dihydrochloride), DMP (dimethyl pimelimidate dihydrochloride), DMS (dimethyl suberimidate dihydrochloride), DTBP (dimethyl 3,3'-dithiobispropionimidate dihydrochloride) and DSP (dithiobis(succinimidyl propionate)).

15. The peptide according to claim 14, wherein the crosslinking agent is DSG (disuccinimidyl glutarate) or DSS (disuccinimidyl suberate).

16. A crosslinked complex of the peptide according to claim 13 and IgG.

17. A method for producing a complex of peptide and IgG, comprising mixing the peptide according to claim 13, thereby crosslinking the peptide modified with the crosslinking agent to IgG.

18. A pharmaceutical composition comprising the peptide according to claim 1.

* * * * *

SEQUENCE LISTING

<160> NUMBER OF SEQ ID NOS: 11

<210> SEQ ID NO 1
<211> LENGTH: 34
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa is lysine, ornithine, cysteine, aspartic
      acid, glutamic acid, 2-amino suberic acid, or diaminopropionic
      acid
<220> FEATURE:
<221> NAME/KEY: misc_feature
<222> LOCATION: (26)..(26)
<223> OTHER INFORMATION: Xaa is arginine, histidine, aspartic acid,
      glutamic acid, serine, threonine, asparagine, glutamine, tyrosine,
      or cysteine
<220> FEATURE:
<221> NAME/KEY: misc_feature
<222> LOCATION: (28)..(28)
<223> OTHER INFORMATION: Xaa is arginine, histidine, aspartic acid,
      glutamic acid, serine, threonine, asparagine, glutamine, tyrosine,
      or cysteine

<400> SEQUENCE: 1

Xaa Asn Met Gln Cys Gln Arg Arg Phe Tyr Glu Ala Leu His Asp Pro
1               5                   10                  15

Asn Leu Asn Glu Glu Gln Arg Asn Ala Xaa Ile Xaa Ser Ile Arg Asp
            20                  25                  30

Asp Cys

<210> SEQ ID NO 2
<211> LENGTH: 35
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa is glycine, alanine, valine, leucine,
      isoleucine, methionine, proline, phenylalanine, tryptophan,
      lysine, ornithine, cysteine aspartic acid, glutamic acid, beta-
      alanine, 2-amino suberic acid, diaminopropionic acid or
      NH2-(PEG)n-CO(n=1-50)
<220> FEATURE:
<221> NAME/KEY: misc_feature
<222> LOCATION: (27)..(27)
<223> OTHER INFORMATION: Xaa is arginine, histidine, aspartic acid,
      glutamic acid, serine, threonine, asparagine, glutamine, tyrosine,
      or cysteine
<220> FEATURE:
<221> NAME/KEY: misc_feature
<222> LOCATION: (29)..(29)
<223> OTHER INFORMATION: Xaa is arginine, histidine, aspartic acid,
      glutamic acid, serine, threonine, asparagine, glutamine, tyrosine,
      or cysteine

<400> SEQUENCE: 2

Xaa Phe Asn Met Gln Cys Gln Arg Arg Phe Tyr Glu Ala Leu His Asp
1               5                   10                  15

Pro Asn Leu Asn Glu Glu Gln Arg Asn Ala Xaa Ile Xaa Ser Ile Arg
            20                  25                  30

Asp Asp Cys
        35

<210> SEQ ID NO 3
<211> LENGTH: 34
<212> TYPE: PRT
<213> ORGANISM: Artificial
<220> FEATURE:
<223> OTHER INFORMATION: synthetic

<400> SEQUENCE: 3

Phe Asn Met Gln Cys Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp Cys

<210> SEQ ID NO 4
<211> LENGTH: 34
<212> TYPE: PRT
<213> ORGANISM: Artificial
<220> FEATURE:
<223> OTHER INFORMATION: synthetic

<400> SEQUENCE: 4

Lys Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

<210> SEQ ID NO 5
<211> LENGTH: 35
<212> TYPE: PRT
<213> ORGANISM: Artificial
<220> FEATURE:
<223> OTHER INFORMATION: synthetic

<400> SEQUENCE: 5

Gly Phe Asn Met Gln Cys Gln Lys Arg Phe Tyr Glu Ala Leu His Asp
1               5                   10                  15

Pro Asn Leu Asn Glu Glu Gln Arg Asn Ala Arg Ile Arg Ser Ile Arg
            20                  25                  30

Asp Asp Cys
        35

<210> SEQ ID NO 6
<211> LENGTH: 34
<212> TYPE: PRT
<213> ORGANISM: Artificial
<220> FEATURE:
<223> OTHER INFORMATION: synthetic

<400> SEQUENCE: 6

Lys Asn Met Gln Cys Gln Lys Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 7
<211> LENGTH: 35
<212> TYPE: PRT
<213> ORGANISM: Artificial
<220> FEATURE:
<223> OTHER INFORMATION: synthetic

<400> SEQUENCE: 7

Gly Phe Asn Met Gln Cys Gln Arg Arg Phe Tyr Glu Ala Leu His Asp
1               5                   10                  15

Pro Asn Leu Asn Glu Glu Gln Arg Asn Ala Arg Ile Arg Ser Ile Arg
            20                  25                  30

Asp Asp Cys
        35

<210> SEQ ID NO 8
<211> LENGTH: 110
<212> TYPE: PRT
<213> ORGANISM: Homo sapiens

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His

```
                65                  70                  75                  80
Gln Asp Trp Leu Asn Gly Lys Glu Tyr Lys Cys Lys Val Ser Asn Lys
                    85                  90                  95
Ala Leu Pro Ala Pro Ile Glu Lys Thr Ile Ser Lys Ala Lys
                    100                 105                 110

<210> SEQ ID NO 9
<211> LENGTH: 34
<212> TYPE: PRT
<213> ORGANISM: Artificial
<220> FEATURE:
<223> OTHER INFORMATION: synthetic

<400> SEQUENCE: 9

Phe Asn Met Gln Cys Gln Arg Arg Phe Tyr Glu Ala Leu His Asp Pro
1               5                   10                  15
Asn Leu Asn Glu Glu Gln Arg Asn Ala Arg Ile Arg Ser Ile Arg Asp
                20                  25                  30
Asp Cys

<210> SEQ ID NO 10
<211> LENGTH: 33
<212> TYPE: PRT
<213> ORGANISM: Artificial
<220> FEATURE:
<223> OTHER INFORMATION: synthetic

<400> SEQUENCE: 10

Phe Asn Met Gln Gln Gln Arg Arg Phe Tyr Glu Ala Leu His Asp Pro
1               5                   10                  15
Asn Leu Asn Glu Glu Gln Arg Asn Ala Arg Ile Arg Ser Ile Arg Asp
                20                  25                  30
Asp

<210> SEQ ID NO 11
<211> LENGTH: 35
<212> TYPE: PRT
<213> ORGANISM: Artificial
<220> FEATURE:
<223> OTHER INFORMATION: synthetic

<400> SEQUENCE: 11

Gly Lys Asn Met Gln Cys Gln Arg Arg Phe Tyr Glu Ala Leu His Asp
1               5                   10                  15
Pro Asn Leu Asn Glu Glu Gln Arg Asn Ala Arg Ile Arg Ser Ile Arg
                20                  25                  30
Asp Asp Cys
        35
```